(12) United States Patent
Swedish et al.

(10) Patent No.: US 9,662,014 B2
(45) Date of Patent: May 30, 2017

(54) METHODS AND APPARATUS FOR VISUAL CUES FOR EYE ALIGNMENT

(71) Applicant: Massachusetts Institute of Technology, Cambridge, MA (US)

(72) Inventors: Tristan Swedish, Cambridge, MA (US); Karin Roesch, Cambridge, MA (US); Ramesh Raskar, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/099,270

(22) Filed: Apr. 14, 2016

(65) Prior Publication Data

US 2016/0302665 A1 Oct. 20, 2016

Related U.S. Application Data

(60) Provisional application No. 62/148,746, filed on Apr. 17, 2015.

(51) Int. Cl.
*A61B 3/14* (2006.01)
*A61B 3/00* (2006.01)
(Continued)

(52) U.S. Cl.
CPC ............ *A61B 3/152* (2013.01); *A61B 3/0025* (2013.01); *A61B 3/0033* (2013.01);
(Continued)

(58) Field of Classification Search
USPC .................................................. 351/200–246
See application file for complete search history.

(56) References Cited

U.S. PATENT DOCUMENTS 8,767,305 B2 7/2014 Spitzer et al.
8,836,778 B2 9/2014 Ignatovich et al.
(Continued)

FOREIGN PATENT DOCUMENTS

WO 2016004385 A1 1/2016

OTHER PUBLICATIONS

Dodgson, N., Analysis of the viewing zone of multiview autostereoscopic displays; published in Proc. SPIE 4660, Stereoscopic Displays and Virtual Reality Systems IX, 254 (May 24, 2002); doi:10.1117/12.468040.
(Continued)

*Primary Examiner* — Mohammed Hasan
(74) *Attorney, Agent, or Firm* — Stephen R. Otis

(57) ABSTRACT

A retinal imaging device includes a camera, a light source, a projector, an I/O device and a computer. The projector emits two sets of light rays, such that one set of rays lies on an exterior surface of a first cone, and the other set of rays lie on an exterior surface of a second cone. The user adjusts the position of his or her eye relative to the camera, until the rays form a full, undistorted target image on the retina. This full, undistorted image is only seen when the pupil of the eye is positioned in the intersection of the first and second cones, and the eye is thus aligned with the camera. The user provides input, via the I/O device, that the user is seeing this image. The computer then instructs the camera to capture retinal images and the light source to simultaneously illuminate the retina.

20 Claims, 14 Drawing Sheets

(51) Int. Cl.
    *A61B 3/15*    (2006.01)
    *A61B 3/12*    (2006.01)
(52) U.S. Cl.
    CPC .......... *A61B 3/0041* (2013.01); *A61B 3/0091* (2013.01); *A61B 3/12* (2013.01)

(56) References Cited

U.S. PATENT DOCUMENTS

| 9,060,718 B2* | 6/2015 | Lawson ............... A61B 3/0091 |
| 9,295,388 B2* | 3/2016 | Lawson ............... A61B 3/0091 |
| 2014/0022270 A1 | 1/2014 | Rice-Jones et al. |

OTHER PUBLICATIONS

Hastings, A., Eye Box Performance Parameters for Non Pupil Forming Head/Helmet Mounted Displays, Dec. 6, 2006, fp.optics.arizona.edu/optomech/student%20reports/tutorials/HastingsTutorial1.doc.

Lanman, D., et al., Near-Eye Light Field Displays, published in ACM SIGGRAPH 2013 Emerging Technologies, Jul. 2013.

* cited by examiner

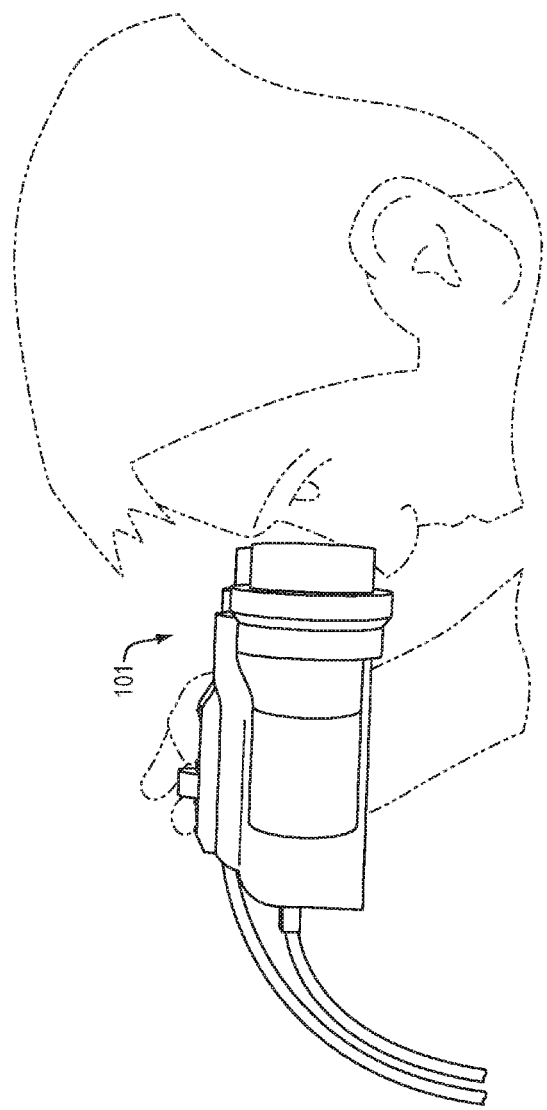
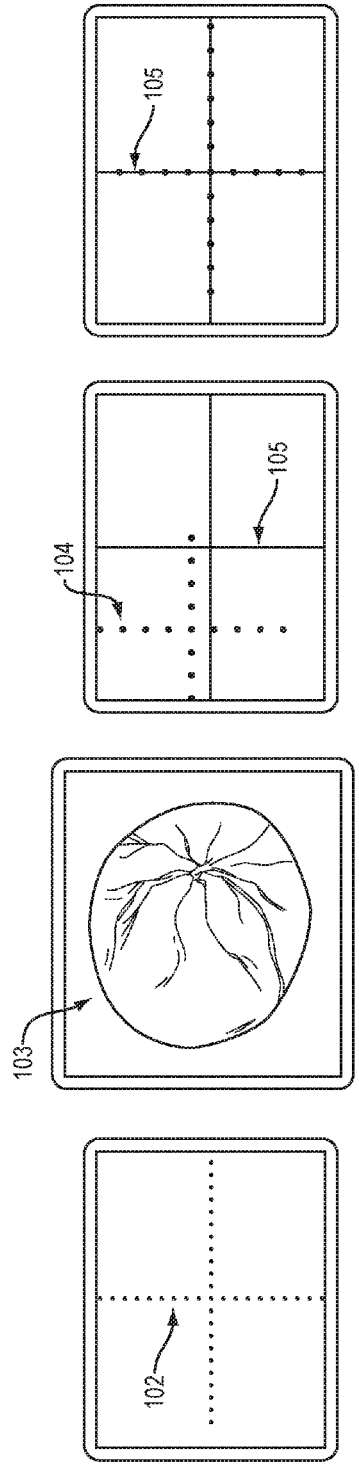

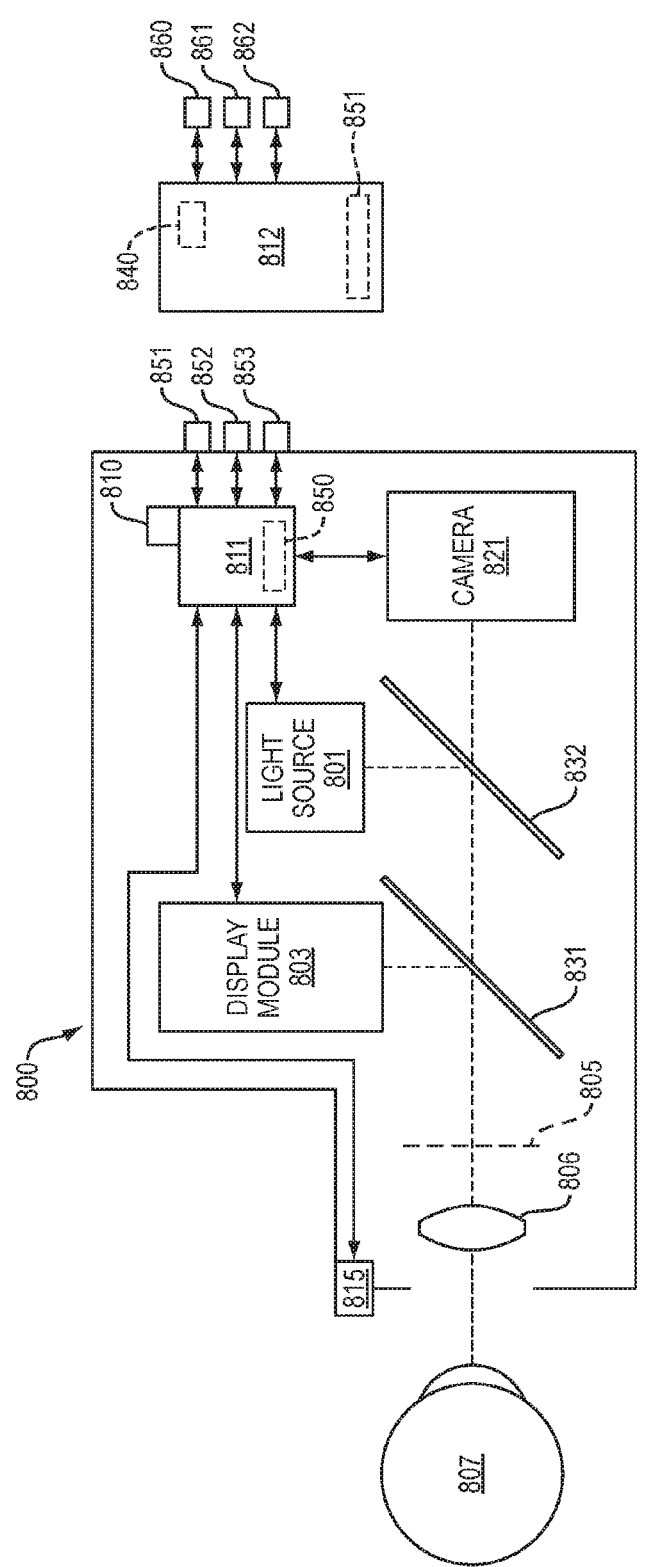

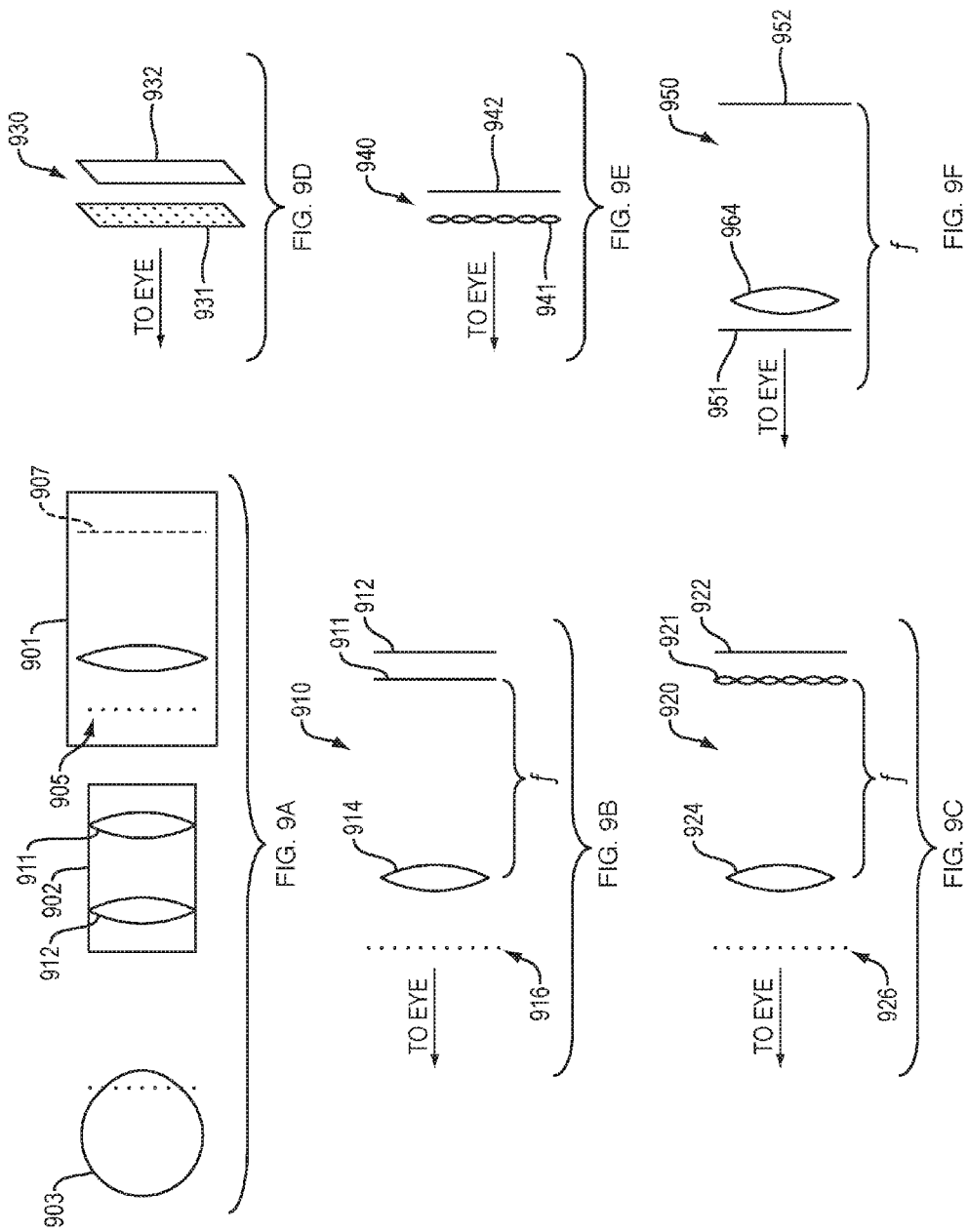

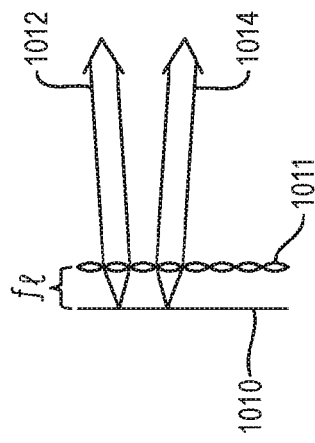
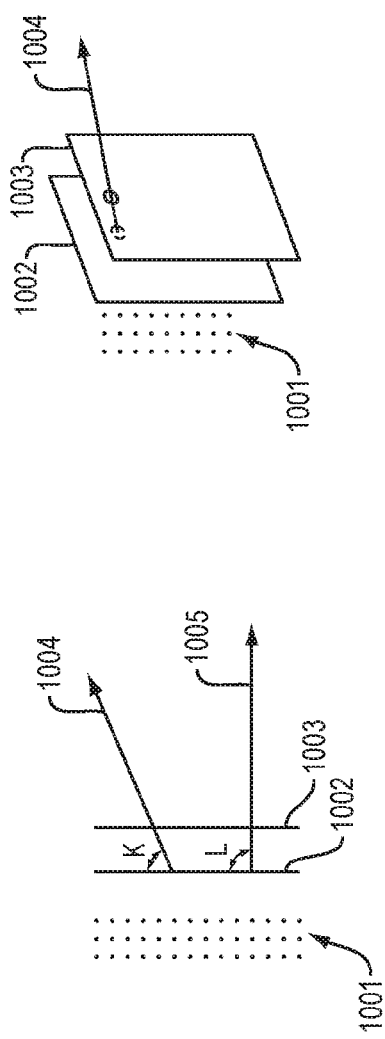
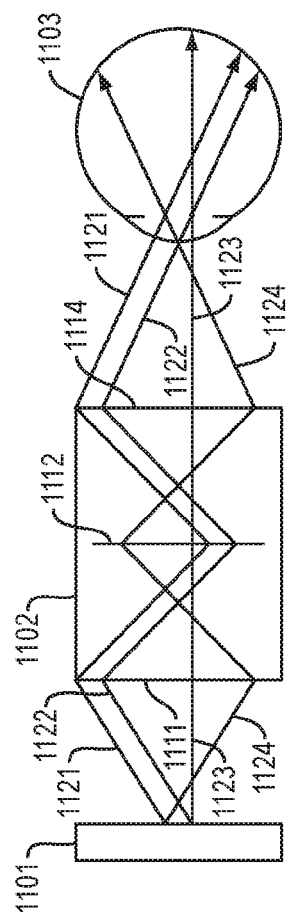

METHODS AND APPARATUS FOR VISUAL CUES FOR EYE ALIGNMENT

RELATED APPLICATION

This application claims the benefit of Provisional Application No. 62/148,746, filed Apr. 17, 2015, the entire disclosure of which is incorporated herein by reference.

STATEMENT REGARDING FEDERALLY SPONSORED RESEARCH OR DEVELOPMENT

This invention was made with government support under Contract No. W911NF-14-1-0014 awarded by the Army Research Office. The government has certain rights in the invention.

FIELD OF TECHNOLOGY

The present invention relates generally to visual cues for eye alignment.

SUMMARY

A challenge in retinal imaging is ensuring that the eye is properly positioned—in 3D spatial coordinates and in direction of gaze—in order for the camera to take images of the retina. This challenge is particularly acute when self-imaging the retina—that is, when a single user employs an imaging system to image the retina of one of his or her own eyes.

With conventional retinal imaging devices, it is difficult for a single user to operate a device that captures images of the user's own eye. This is because, with conventional devices, the user lacks visual cues that would assist the user in properly locating the user's own eye (in terms of 3D spatial position and direction of gaze) relative to the camera of the imaging device.

In illustrative implementations of this invention, this problem is solved by displaying a set of light rays that appear—to a user's eye—to be a desired target pattern of light only when the user's eye is properly positioned relative to the camera. If the eye is not properly positioned relative to the camera, then the set of light rays appears to the user's eye as a truncated or distorted version of the target pattern, or the target pattern is not visible to the user.

In illustrative implementations of this invention, a retinal imaging device includes a camera, a light source, a projector, an I/O device and a computer. The projector emits two sets of light rays, such that one set of rays lies on an exterior surface of a first cone, and the other set of rays lie on an exterior surface of a second cone. The user adjusts the position of his or her eye relative to the camera, until the rays form a full, undistorted target image on the retina. This full, undistorted image is only seen when the pupil of the eye is positioned in the intersection of the first and second cones, and the eye is thus aligned with the camera. The user provides input, via the I/O device, that the user is seeing this image. The computer then instructs the camera to capture retinal images and the light source to simultaneously illuminate the retina.

In illustrative implementations, a handheld retinal imaging device displays visual cues that help a user align his or her own eye with the camera in the device. The handheld device includes a display module for producing the visual cues, a light source for illuminating the eye, and a camera for taking retinal images. The user holds the handheld device up to an eye of the user. The display module onboard the handheld device displays visual cues to the user. The user moves the device until the user sees a desired target pattern. At that point, the eye is then properly positioned relative to the camera. The user provides input to the handheld device, indicating that the user sees the pattern. This input triggers the camera to capture centered, in-focus images of the retina, while the light source illuminates the retina.

The visual cues make it easy for a user to properly align his or her eye with a camera, and thus make it practical and easy for a user to self-image his or her retina—that is, without assistance from other people, to use the device to take high-quality images of his or her own retina.

In some implementations of this invention, the visual cues are formed by a double cone pattern of light rays. Specifically, in some implementations, the display module onboard the handheld device emits a double cone pattern of rays that form all or part the target visual pattern. Before entering the eye (and thus before being refracted by the eye), the double cone pattern of rays comprises: (a) multiple light rays that lie on the outer surface of a first geometric cone; and (b) multiple light rays that lie on the outer surface of a second geometric cone.

Alternatively, in some implementations, the visual cues are formed by a single cone pattern of light rays. Specifically, in some implementations, the display module onboard the handheld device emits a single cone pattern of rays that form all or part the target visual pattern. Before entering the eye (and thus before being refracted by the eye), the single cone pattern of rays comprises multiple light rays that lie on the outer boundary of a single cone.

A single cone set of rays provides less visual cues than a double cone set of rays. Thus, with a single cone, it is more likely that a user will move the eye such that the target pattern becomes completely invisible to the user. Once the target pattern is invisible to the user, it is harder for the user to figure out where to move the eye, to position it properly.

A key advantage of a double cone (as opposed to a single cone) set of light rays is that a double cone may provide more visual cues as the user's eye moves away from the best position, thereby providing better feedback regarding the position of user's eye.

In some implementations, the light rays that form the visual cues (that facilitate eye alignment) have a color that is different than the color of illumination used to illuminate the retina for retinal imaging. For example, in some implementations: (a) a "white" light source (i.e., a broad spectrum visible light source) in the retinal imaging device provides illumination while the camera captures images; but (b) the display module emits red light rays that form the visual cues for eye alignment. The red illumination may be created by color filters.

For purposes hereof, to say that an eye is "aligned" with a camera—or that the eye is "properly positioned" relative to the camera—means that the eye is in a position relative to the camera, such that (i) the camera has an unimpeded view of the retina of the eye (when the eyelids are open), (ii) the eye is gazing at the camera and is centered in the camera's field of view; and (iii) the eye is at a depth from the camera that is suitable for taking focused images of the retina free of reflection artifacts.

As used herein, an "eyebox" means the set of eye positions in which the eye is aligned with the camera.

Unless the context clearly indicates otherwise, as used herein, each "position" of an eye is specified by a total of five coordinates: three spatial coordinates (i.e. 3D spatial coordinates x, y, z) of the centroid of the eye and by two angular coordinates for the direction of gaze of the eye.

In some implementations of this invention, the outer boundary of the 3D spatial coordinates of the eyebox coincides with the outer boundary of the region that is the intersection (i.e., overlap) of two geometric right circular cones.

In illustrative implementations, the display module emits a set of light rays that form a visual cue to the user. The set of light rays are spatially arranged such that, when the pupil of the eye is in the eyebox and the eye is focused at optical infinity, each respective light ray in the set strikes a pupillary plane at a unique point in the pupillary plane and strikes the retina at a unique point in the retina.

Furthermore, in illustrative implementations, the set of light rays (that are emitted by the display module) are spatially arranged such that, when the pupil of the eye is in the eyebox and the eye is focused at infinity, there is a one-to-one mapping between (i) the direction at which a ray in the set strikes the pupillary plane and (ii) the point on the retina at which the ray hits the retina. Thus, when the pupil is in the eyebox and the eye is focused at optical infinity, the point in the retina that is hit by a light ray in the set is a function of the direction at which the ray strikes the pupillary plane.

In some implementations, sensors provide feedback that helps control the display module. For example, in some cases, a computer: (a) determines, based on sensor data, an approximate position of the eye, and (b) based on this computed position, outputs signals that cause the display module to adjust the visual cues provided to the user. For example, the visual cues may be adjusted by altering the angle at which a cone of light rays converges to an apex. Or, the visual cues may be adjusted to display a graphical arrow pointing in a lateral direction that the eye should be moved (or that the retinal imaging device should be moved). Or, the visual cues may be adjusted to display graphics that indicate whether the eye should move closer to or farther from the camera, or stay at the same depth relative to the camera.

In illustrative implementations, once a user moves the pupil into the eyebox, the user sees the full, undistorted target display produced by the display module. The user provides feedback, such as by pushing a button or touching an icon on a touch screen. The feedback indicates that the user sees the full, undistorted target display (and thus that the pupil is in the eyebox). In response to this user feedback, a computer outputs signals that cause the camera to take one or more images of the retina.

The description of the present invention in the Summary and Abstract sections hereof is just a summary. It is intended only to give a general introduction to some illustrative implementations of this invention. It does not describe all of the details and variations of this invention. Likewise, the description of this invention in the Field of Technology section is not limiting; instead it identifies, in a general, non-exclusive manner, a technology to which exemplary implementations of this invention generally relate. Likewise, the Title of this document does not limit the invention in any way; instead the Title is merely a general, non-exclusive way of referring to this invention. This invention may be implemented in many other ways.

BRIEF DESCRIPTION OF THE DRAWINGS

FIG. 1A shows a user holding a retinal imaging device.
FIG. 1B shows a visual pattern of dots displayed by the retinal imaging device.

FIG. 1C shows an image captured by a digital camera in the retinal imaging device.
FIG. 1D shows a visual pattern of dots, as perceived by a user, when the test eye is not properly positioned relative to the camera.
FIG. 1E shows a visual pattern of dots, as perceived by a user, when the test eye is properly positioned relative to the camera.
FIG. 8 shows hardware components of a retinal imaging device.
FIG. 9A shows a display module that is onboard the retinal imaging device.
FIGS. 9B, 9C, 9D, 9E, and 9F show examples of a projector, which is part of the display module.
FIGS. 10A, 10B, and 10C show examples of hardware for producing a light field.
FIG. 11 shows an example of relay optics.

Figure 2:
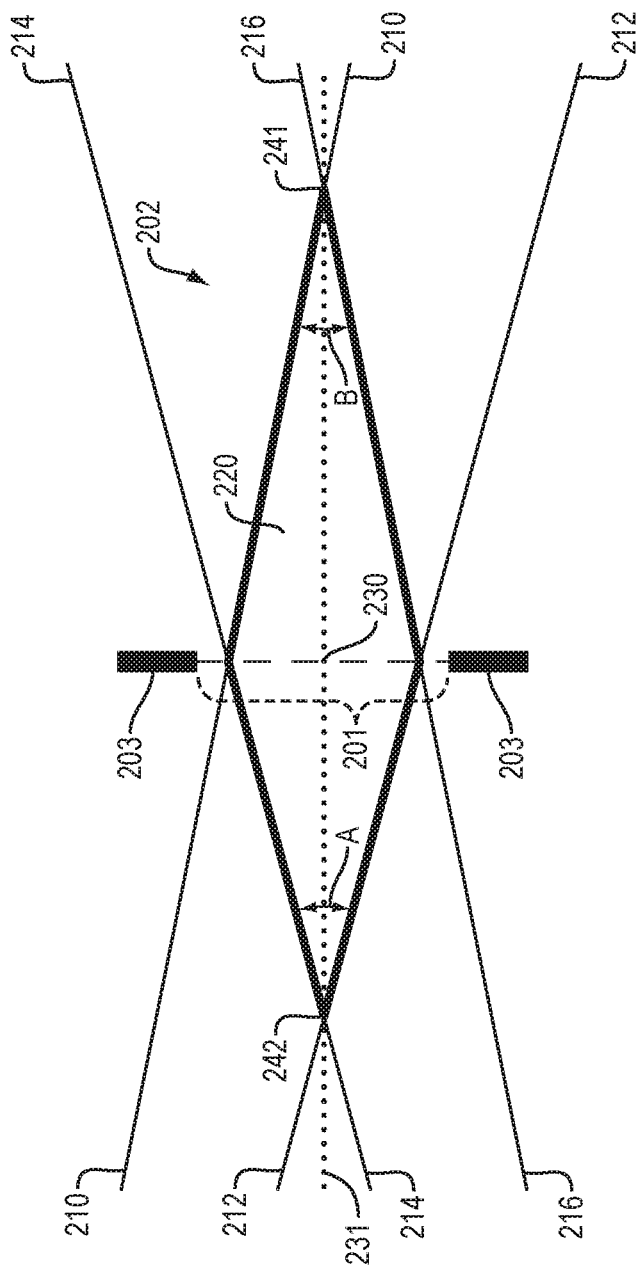
FIG. 2 is a diagram of a double cone set of light rays.

The above Figures show some illustrative implementations of this invention, or provide information that relates to those implementations. However, this invention may be implemented in many other ways.

DETAILED DESCRIPTION

General

FIGS. 1A-1E provide an overview of the operation of a retinal imaging device 101, in an illustrative implementation of this invention. In the example shown in FIGS. 1A-1E, a user holds the device 101 and moves the device relative to the user's eye until a complete target pattern 102 becomes visible, without distortion, to the user's eye. When the eye is not properly positioned, the user's eye may see only a truncated, off-center version 104 of the target pattern. When the eye is properly positioned, the complete, centered, undistorted target pattern (e.g., 102) is visible to the user's eye. Once the eye is properly positioned, the camera captures one or more images (e.g., 103) of the retina of the eye.

In some implementations (such as FIGS. 1D and 1E), the imaging device also displays a static visual pattern, such as the static "crosshairs" pattern 105 shown in FIGS. 1D and 1E. The user positions the eye such that the target pattern 101 appears—to the user's eye— to be aligned with the static visual feature (e.g., 105). When this occurs, the eye is properly positioned for retinal imaging.

In illustrative implementations of this invention, the eyebox of the retinal imaging device coincides with a region that is the intersection (i.e., overlap) of two geometric right circular cones.

In some implementations of this invention, a projector emits a "double cone set of light rays" that forms all or part the target visual pattern.

FIG. 2 shows a diagram of a double cone set of light rays, in an illustrative implementation of this invention. In FIG. 2, light passes through pupil 201 into the interior 202 of an eye. The sclera 203 blocks other light from entering the eye. A display module in the imaging device (not shown in FIG. 2) produces a first set of multiple light rays that lie on an external surface of a first geometric cone and a second set of multiple light rays that lie on an external surface of a second geometric cone. The first set of light rays includes rays 210 and 216. The second set of light rays includes light rays 212, 214.

The 3D eyebox is located at the intersection (overlap) of the two geometric cones. Specifically, the eyebox 220 is the 3D region that consists of the intersection of a first 3D cone and a second 3D cone. In FIG. 2, the first 3D cone has an apex 241, and extends (from apex 241) towards the left side of FIG. 2. Light rays 210 and 216 lie on the exterior surface of the first 3D cone. The second 3D cone has an apex 242, and extends (from apex 242) towards the right side of FIG. 2. Light rays 212 and 214 lie on the exterior surface of the second 3D cone.

In FIG. 2, the 2D cross-section of eyebox 220 is a convex quadrilateral that does not have any parallel sides and that appears roughly similar to a diamond. In FIG. 2, the upper left, upper right, lower left and lower right sides of this quadrilateral (the 2D cross-section of eyebox 220) are formed by parts of light rays 214, 210, 212, and 216, respectively.

In FIG. 2, the pupillary center 230 (i.e., center of the pupil of the eye) is located on the optical axis 231 of the camera of the retinal imaging device. The pupillary center may move to a limited extent without exiting the eyebox. For example, the pupillary center may—without exiting the eyebox—move to a limited extent nearer to or farther from the eye (along optical axis 231). Likewise, the pupillary center may—without exiting the eyebox—move to a limited extent laterally. For example, the lateral movement may be along a line that is perpendicular to optical axis 231.

In FIG. 2, angles A and B are not equal.

For clarity of presentation, in FIGS. 2, 3A, 3B, 3C, 4A, 4C, 4E, 4G, 5A, 5C, 5E, 5G, 6A, 6B, 6C, and 6E, light rays are shown without giving effect to refraction by eye structures such as the crystalline lens. In actual practice, however, the light rays would be refracted by the eye and the shape of the eyebox would be altered accordingly.

In some implementations of this invention, a pair of spatial light modulators (SLMs) produce a set of light rays that form the visual cues that assist the user in aligning his or her own eye. For example, in some cases, each SLM comprises a static mask (such as a pinhole mask). In other cases, each SLM is a dynamic display, such as a liquid crystal display (LCD). In some cases, the SLMs are backlit and produce a set of light rays that form the visual cues. In some cases, the light rays lie on the exterior surface of one or more cones.

Figure 3A:
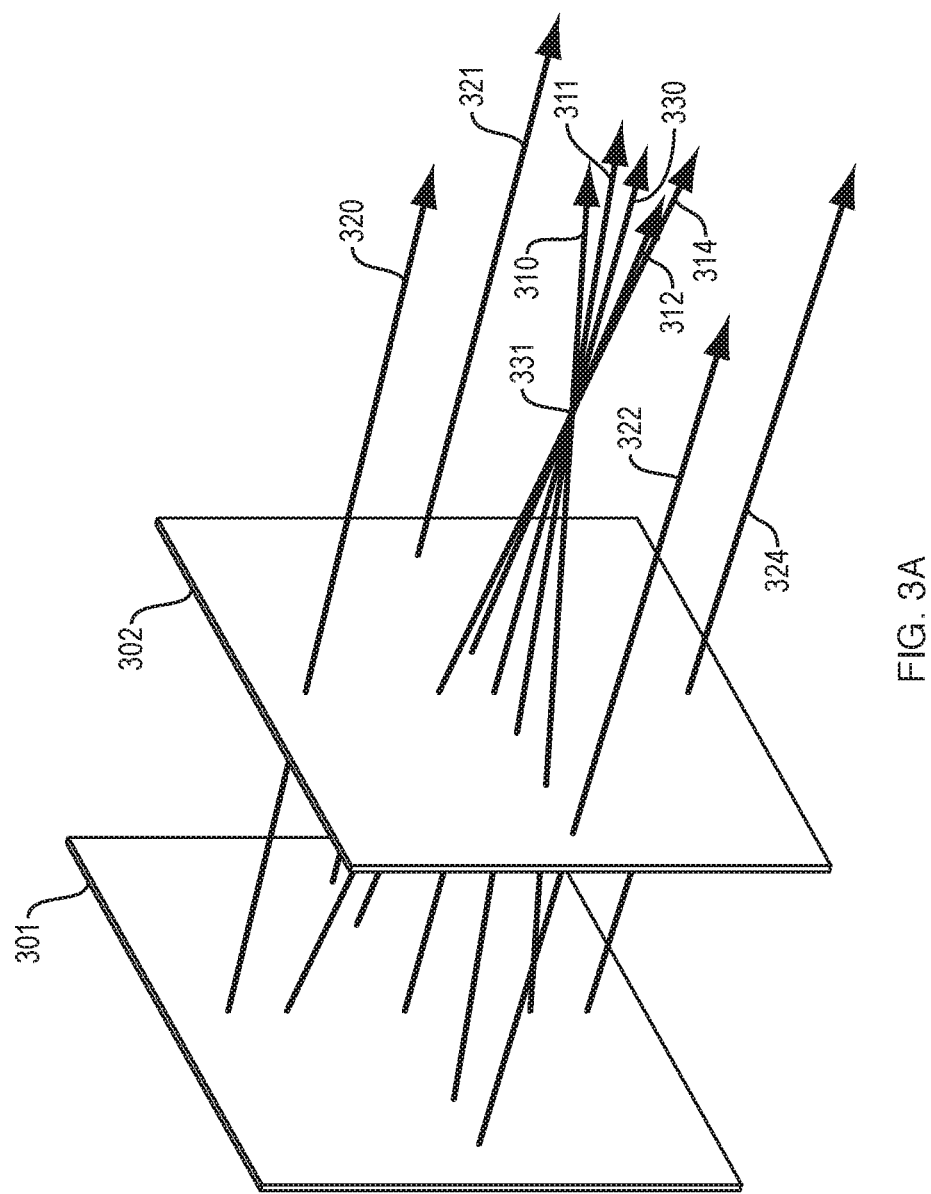
FIG. 3A shows two pinhole masks producing a pattern of light rays.
Figure 3B:
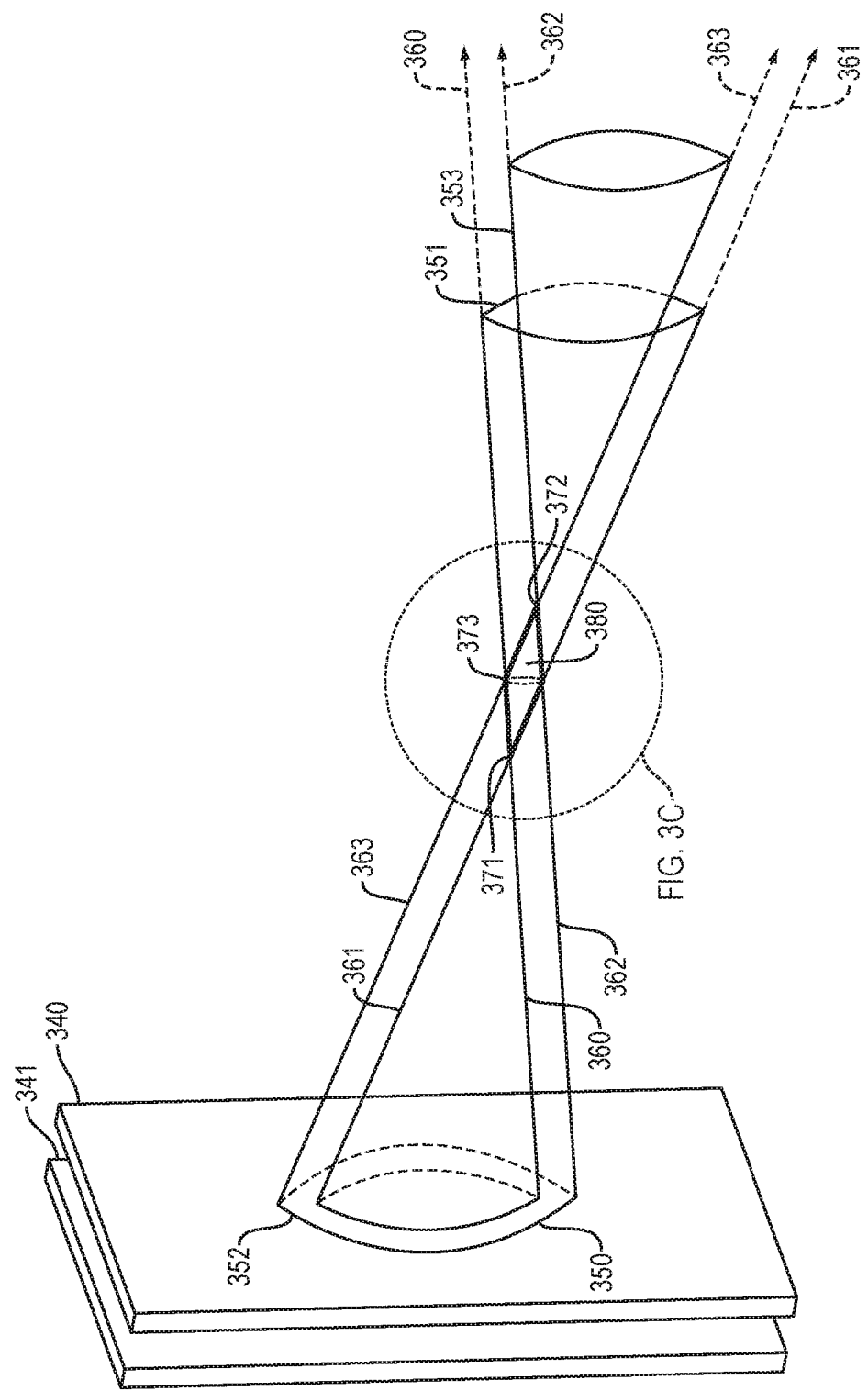
FIG. 3B is another diagram of a double cone set of light rays.

FIGS. 3A and 3B each show a pair of SLMS producing a double cone set of light rays, in an illustrative implementation of this invention.

FIG. 3A shows two pinhole masks 301, 302 that together produce a first set of light rays 310, 311, 312, 314, a second set of light rays 320, 321, 322, 324, and a central light ray 330. The first set of light rays lie on the exterior surface of a first cone and the second set of light rays lie on the exterior surface of a second cone.

In FIG. 3A, a first cone has an apex 331 and extends (from apex 331) towards the right side of FIG. 3A. The first set of light rays 310, 311, 312, 314 lie on the exterior surface of the first cone. In FIG. 3A, the second set of rays 320, 321, 322, 324 converge slowly to the apex of the second cone. But the apex of the second cone is so far away that it is not shown in FIG. 3A. (For clarity of presentation, in FIG. 3A, the light rays in the second cone are shown as converging slowly to an apex. This makes the individual light rays easier to see in FIG. 3A. However, in actual practice, the second cone may converge to an apex more rapidly than shown in FIG. 3A).

FIG. 3B shows two SLMs producing another double cone set of light rays. In FIG. 3B, two spatial light modulators 340, 341 together produce: (a) a first set of light rays that lie on the exterior surface of a first cone; and (b) a second set of light rays that lie on the exterior surface of a second cone.

In FIG. 3B, eyebox 380 is the 3D region that consists of the intersection of a first 3D cone 351 and a second 3D cone 352. The first 3D cone 351 has an apex at point 371 and extends (from apex 371) towards the right side of FIG. 3B. Light rays 360 and 361 lie on an exterior surface of the first cone. The second 3D cone 352 has an apex at point 372 and extends (from apex 372) towards the left side of FIG. 3B. Light rays 362 and 363 lie on an exterior surface of the second cone.

In FIG. 3B, eyebox 380 is widest at circular area 373. Eyebox 380 is closest to the SLMs 340, 341 at apex 371 and is furthest from the SLMs at apex 372.

Figure 3C:
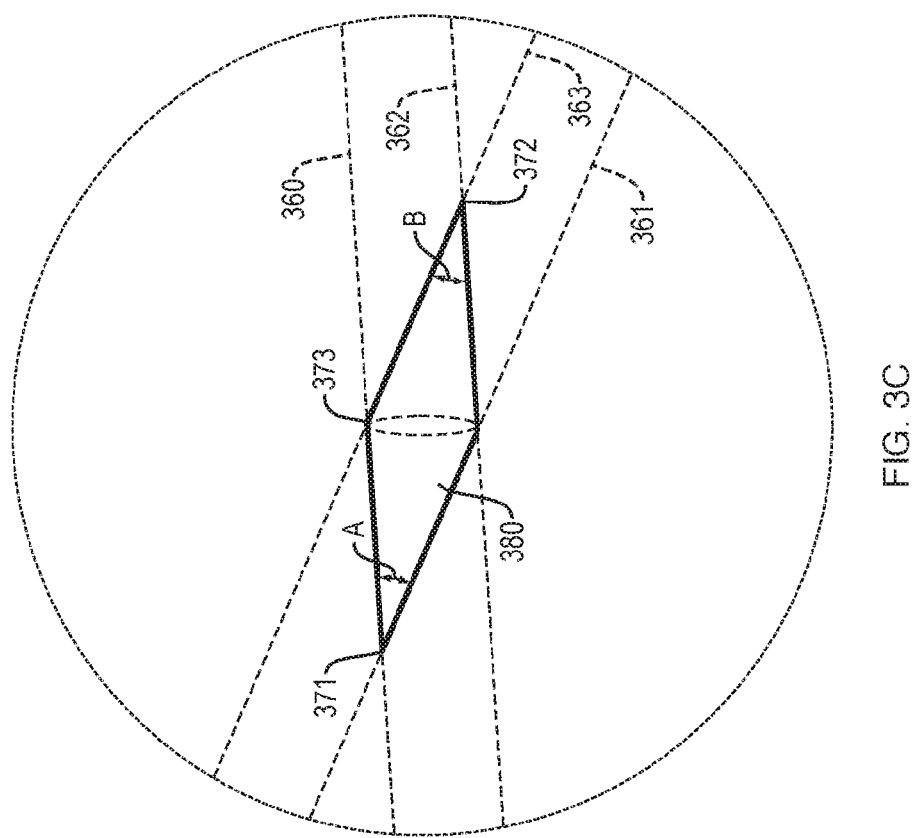
FIG. 3C is a close-up diagram of a double cone set of light rays.

FIG. 3C is a close-up diagram of double cone set of light rays shown in FIG. 3B.

In the example shown in FIG. 3C, the angle at which the first and second cones converge to an apex are not equal, and thus angles A and B are not equal to each other. In some implementations, making these angles A and B unequal helps to ensure that, when the eye is focused at infinity, each of the light rays that are produced by the display module hit the pupil at a unique location and hit the retina at a unique location.

In illustrative implementations of this invention, a double cone (or single cone) set of light rays provides a visual cue that changes, depending on where the user's eye is positioned. If the eye is properly positioned, the user sees the full, undistorted target pattern. As the eye moves away from the proper position, the target pattern appears truncated, or off-center, or distorted. At some point, if the eye is too far away from the proper position, then the target pattern becomes invisible.

FIGS. 4A-4H and 5A-5H show how eye position impacts the appearance of a target visual pattern, in illustrative implementations of this invention. In FIGS. 4A-4H, the target visual pattern is formed by a double cone set of light rays. In FIGS. 6A-6H, the target visual pattern is formed by a single cone set of light rays.

Eye Interaction with Double Cone Pattern of Light Rays

FIGS. 4A to 4H show examples of how a double cone pattern of light rays interacts with an eye, in an illustrative implementation of this invention. In FIGS. 4A to 4H, different eye positions affect which light rays enter the eye and what visual pattern is seen by the eye. The position of the eye relative to the camera of the retinal imaging device is: (a) in FIG. 4A, properly positioned; (b) in FIG. 4C, laterally off-center; (c) in FIG. 4E, too far away; and (d) in FIG. 4G, too close. FIGS. 4B, 4D, 4F, 4H show a pattern of dots in an image that is formed at the retina of the eye (and thus perceived by a user), when the eye is positioned as shown in FIGS. 4A, 4C, 4E and 4G, respectively.

In FIGS. 4A, 4C, 4D, and 4G, the retinal imaging device includes a display module. The display module comprises a projector 401 and relay optics 402. Projector 401 emits a double cone pattern of light rays. The relay optics 402 then relay these light rays. For example, light rays 410, 411, 412, 414 emerge from the relay optics 402 and travel toward the eye 403.

Figure 4A:
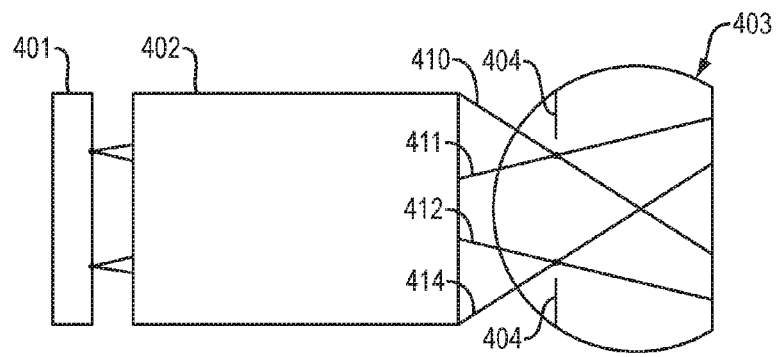
FIGS. 4A, 4B, 4C, 4D, 4E, 4F, 4G, and 4H show examples of how a double cone pattern of light rays interacts with an eye.
Figure 4B:
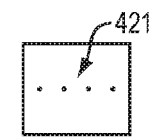

In the example shown in FIG. 4A, the eye 403 is properly positioned relative to the camera of the imaging device, and thus light rays 410, 411, 412, 414: (a) are not blocked by the sclera 404 of the eye; and (b) instead pass through the pupil 405 into the eye. Thus, the user sees a pattern of four dots 421, as shown in FIG. 4B.

Figure 4C:
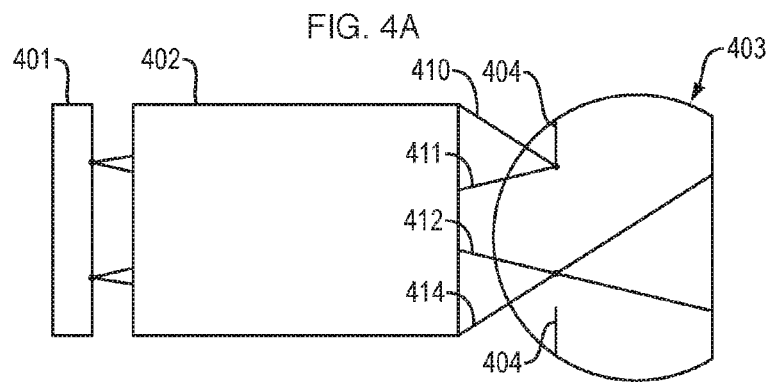
Figure 4D:
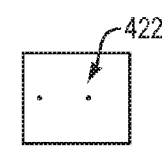

In the example shown in FIG. 4C, the eye 403 is laterally off-center relative to the camera of the imaging device, causing light rays 410, 411 to be blocked by the sclera 404 of the eye. However, light rays 412, 414 pass through the pupil into the eye. Thus, the user sees a pattern of two dots 422, as shown in FIG. 4D.

Figure 4E:
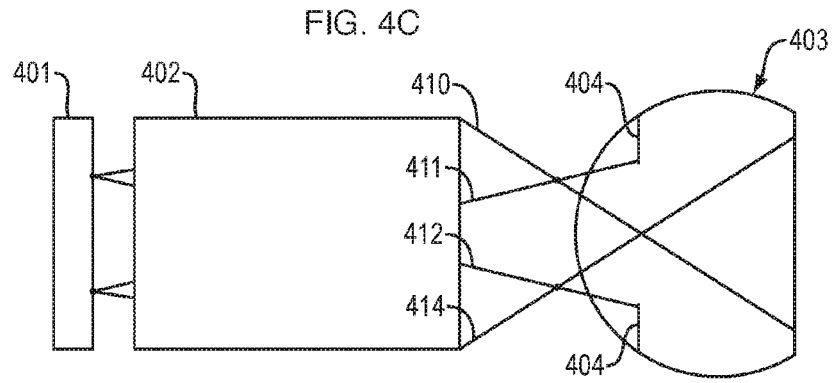
Figure 4F:
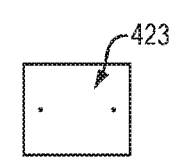

In the example shown in FIG. 4E, the eye 403 is too far away from the camera of the imaging device, causing light rays 411, 412 to be blocked by the sclera 404 of the eye. However, light rays 410, 414 pass through the pupil into the eye. Thus, the user sees a pattern of two dots 423, as shown in FIG. 4F.

Figure 4G:
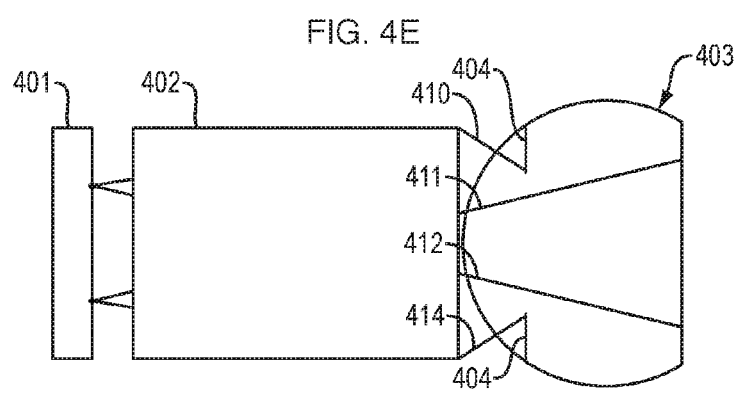
Figure 4H:
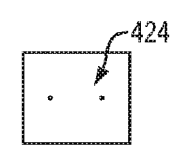

In the example shown in FIG. 4G, the eye 403 is too close to the camera of the imaging device, causing light rays 410, 414 to be blocked by the sclera 404 of the eye. However, light rays 411, 412 pass through the pupil into the eye. Thus, the user sees a pattern of two dots 424, as shown in FIG. 4H.

Eye Interaction with Single Cone Pattern of Light Rays

FIGS. 5A to 5H show examples of how a single cone pattern of light rays interacts with an eye, in an illustrative implementation of this invention. In FIGS. 5A to 5H, different eye positions affect which light rays enter the eye and what visual pattern is seen by the eye. The position of the eye relative to the camera of the retinal imaging device is: (a) in FIG. 5A, properly positioned; (b) in FIG. 5C, laterally off-center; (c) in FIG. 5E, too far away; and (d) in FIG. 5G, too close. FIGS. 5B, 5D, 5F, 5H show a pattern of dots in an image that is formed at the retina of the eye (and thus perceived by a user), when the eye is positioned as shown in FIGS. 5A, 5C, 5E and 5G, respectively.

In FIGS. 5A, 5C, 5D, and 5G, the retinal imaging device includes a display module. The display module comprises a projector 501 and relay optics 502. Projector 501 emits a single cone pattern of light rays, which are relayed to the eye by relay optics 502. Light rays 510, 511 emerge from the relay optics 502 and travel toward the eye 503.

Figure 5A:
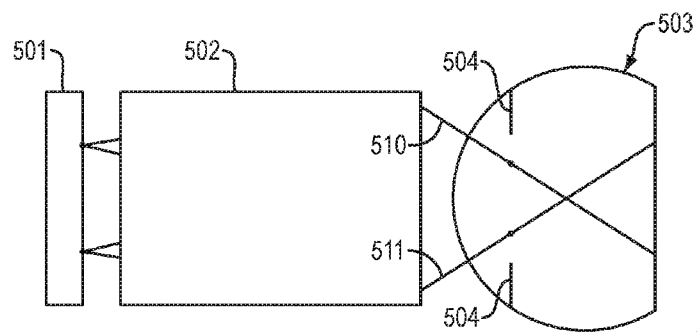
FIGS. 5A, 5B, 5C, 5D, 5E, 5F, 5G, and 5H show examples of how a single cone pattern of light rays interacts with an eye.
Figure 5B:
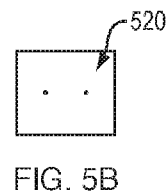

In the example shown in FIG. 5A, the eye 503 is properly positioned relative to the camera of the imaging device, and thus light rays 510, 511: (a) are not blocked by the sclera 504 of the eye; and (b) instead pass through the pupil into the eye. Thus, the user sees a pattern of two dots 520, as shown in FIG. 5B.

Figure 5C:
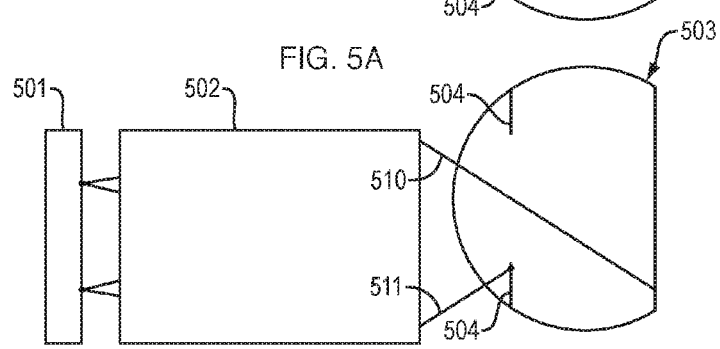
Figure 5D:
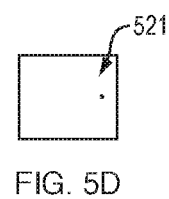

In the example shown in FIG. 5C, the eye 503 is laterally off-center relative to the camera of the imaging device, causing light ray 511 to be blocked by the sclera 504 of the eye. However, light ray 510 passes through the pupil into the eye. Thus, the user sees a pattern of one dot 521, as shown in FIG. 5D.

Figure 5E:
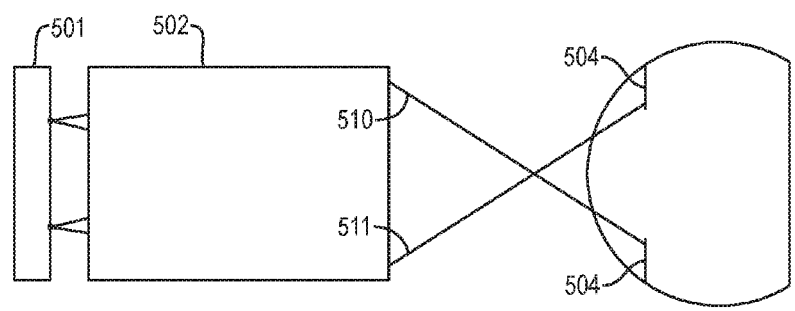
Figure 5F:
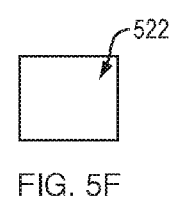

In the example shown in FIG. 5E, the eye 503 is too far away from the camera of the imaging device, causing light rays 510, 511 to be blocked by the sclera 504 of the eye. Thus, the user sees a pattern of no dots 522, as shown in FIG. 5F.

Figure 5G:
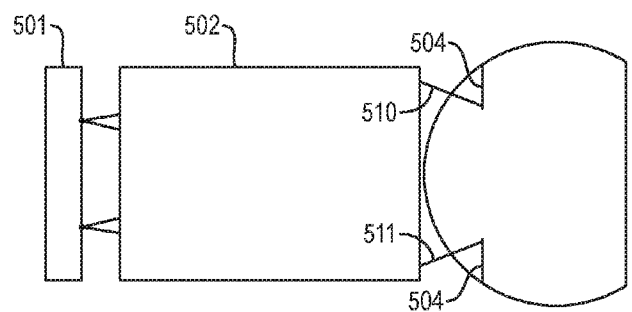
Figure 5H:
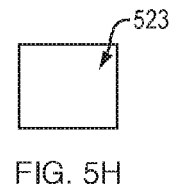

In the example shown in FIG. 5G, the eye 503 is too close to the camera of the imaging device, causing light rays 510, 511 to be blocked by the sclera 504 of the eye. Thus, the user sees a pattern of no dots 522, as shown in FIG. 5H.

Impact of Lateral and Rotational Position of Eye

FIGS. 6A-6D show how the eye's position may affect which light rays enter the eye, in an illustrative implementation of this invention. In FIGS. 6A-6D, two light rays 601, 602 are emitted and relayed by a display module of the retinal imaging device. These two light rays 601, 602 travel toward an eye 603. As shown in these Figures, in some instances the rays strike the sclera 604 of the eye, and in other instances the rays pass through the pupil 605 of the eye.

Figure 6A:
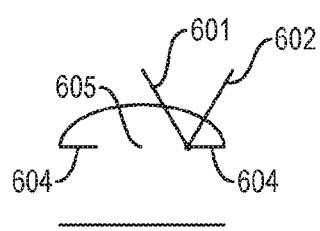
FIGS. 6A, 6B, 6C and 6D show how the eye's position may affect which light rays enter the eye.

In the example shown in FIG. 6A, the eye is laterally off-center relative to the camera of a retinal imaging device. This causes rays 601, 602 to be blocked by the sclera 604.

Figure 6B:
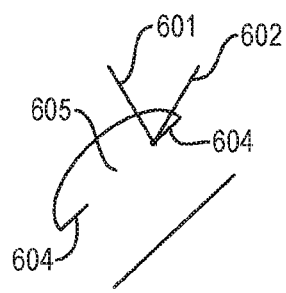

In the example shown in FIG. 6B, the eye is rotationally off-center relative to the camera of a retinal imaging device. Again, this causes rays 601, 602 to be blocked by the sclera 604.

Figure 6C:
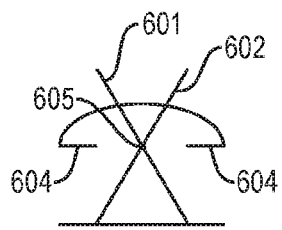
Figure 6D:
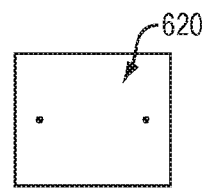

In the example shown in FIG. 6C, the eye is rotationally centered (and otherwise properly positioned) relative to the camera of a retinal imaging device. This allows rays 601, 602 to pass through the pupil 605, and thus the viewer sees the pattern of two dots 620 shown in FIG. 6D.

Figure 6E:
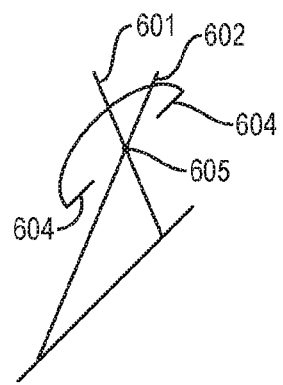
FIG. 6E shows an eye rotationally off-center relative to the camera of a retinal imaging device.
Figure 6F:
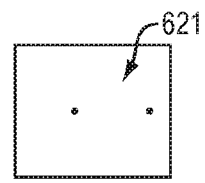
FIG. 6F shows a distorted pattern of two dots.

In the example shown in FIG. 6E, the eye is rotationally off-center relative to the camera of a retinal imaging device. Even though rays 601, 602 pass through the pupil 306, the fact that the eye is rotationally off-center changes where the rays strike the retina. Thus the viewer sees the distorted pattern of two dots 621 shown in FIG. 6F.

In FIGS. 4A, 4C, 4E, 4G, 5A, 5C, 5E, 5G, 6A, 6B, 6C, and 6E, the straight line on the right (or bottom) side of the diagram of the eye symbolizes the so-called retinal plane—that is, a plane in which light would strike the retina if the retina were planar and the eye did not refract light.

Hardware and Functionality

Figure 7:
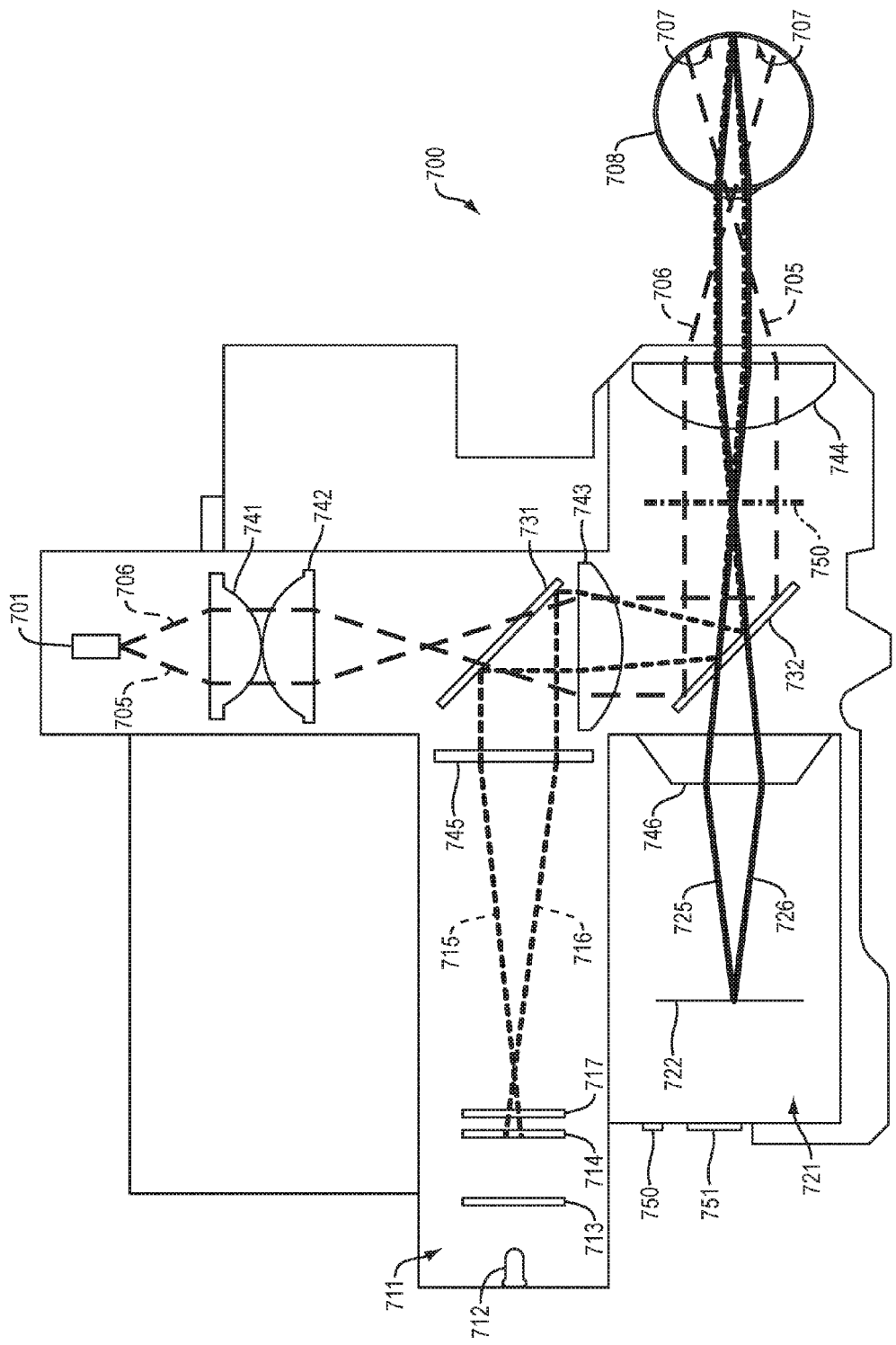
FIG. 7 shows a retinal imaging device.

FIG. 7 shows a retinal imaging device 700, in an illustrative implementation of this invention. The imaging device 700 includes a light source 701, a projector 711, and a camera 721.

Light source 701 emits visible light, which travels to the retina 707 of an eye 708 to illuminate the retina 707 during image capture. Lines 705 and 706 show two paths by which light travels from light source 701 to the retina 707. These light paths 705, 706 each pass through relay lenses 741, 742 pass through beamsplitter 731, pass through relay lens 743, reflect from beamsplitter 732, and pass through lens 744.

Projector 711 emits a light field of light rays that produces a visual pattern that helps a user properly position the eye 708 for retinal imaging by the camera 721. Projector 711 includes an illumination source 712, a diffuser 713, and two spatial light modulators (e.g., pinhole masks) 714, 717. Lines 715 and 716 show two paths by which light travels from the spatial light modulators 714, 717 to the retina 707. These light paths 715, 716 each pass through lens 745, reflect from beamsplitter 731, pass through relay lens 743, reflect from beamsplitter 732, and pass through lens 744.

Digital camera 721 captures images of the retina 707. Camera 721 includes an imaging sensor 722 and one or more lenses 746. Light reflects from the retina 707 and travels to the camera. Lines 725 and 726 show two paths by which light travels from the retina 707 to the imaging sensor 722 of the camera. These light paths pass through lens 744, beamsplitter 732, and lens 746.

The retinal imaging device 700 includes I/O devices 750, 751. For example, the I/O devices 750, 751 may comprise buttons, dials, sliders, or a touch screen. When the user has aligned his or her eye with the camera, the user sees the full, undistorted, target image. The user then provides input, via the I/O devices, that triggers the camera 721 to capture images of the retina 707.

FIG. 8 shows hardware components of a retinal imaging device 800, in an illustrative implementation of this invention. The imaging device 800 includes a light source 801, a display module 803, a camera 821, an onboard computer 811, two beamsplitters 831, 832, the one or more lenses 806, and a wireless communication module 810. The imaging device 800 communicates with an external computer 841 either by wired connection or by a wireless connection. Computers 811, 812 include memory devices 850, 851, respectively.

The display module 803 includes a projector and relay optics. The display module 803 displays a visual pattern that helps the user properly position his or her own eye 805 for retinal imaging. Once the eye is aligned with the camera, the light source 801 illuminates the retina 707 while the camera 821 captures one or more images of the retina.

In some cases, the retinal image device 800 includes one or more other sensors 815 (e.g., time-of-flight or other range-finding sensors) that measure an approximate distance from the device 800 to the eye 807. Based on these measurements, one or more computers (e.g., 811 or 812) adjust a visual display that is visible to the user.

The retinal imaging device 800 includes I/O devices 851, 852, 853, that are onboard the device. For example, I/O devices 851, 852, 853 may comprise buttons, dials, sliders, or a touch screen. When the user has aligned his or her eye with the camera, the user sees the full, undistorted, target image and provides input, via the I/O devices, that triggers the camera 821 to capture images of the retina of the eye 807.

In addition, a user may provide input via I/O devices that are remote from the retinal imaging device 800. For example, remote I/O devices 860, 861, 862 may comprise one or more of a keyboard, computer mouse, graphical user interface, touch screen, and microphone. A user may employ one or more I/O devices (e.g., 851, 852, 853, 861, 862, 863): (a) to provide input that adjusts the operation of the retinal imaging device or that triggers the camera 821 to capture images of the retina; or (b) to receive information outputted by the retinal imaging system.

In some implementations, the light rays that form the visual cues (that facilitate eye alignment) have a color that is different than the color of light used to illuminate the retina for retinal imaging. For example, in some implementations, a light source (e.g., 701, 801) comprises a white light source. This light source (e.g., 701, 801) provides illumination while the camera captures images. However, the display module (e.g., 711, 803) produce light rays that have a different color. For example, the display module (e.g., 711, 803) may include color filters that cause the light rays produced by the display module to be red. Alternatively, in some cases, the display module may output a number of different colors of light rays. These different-colored light rays produce multiple colors of visual cues that facilitate eye alignment.

FIG. 9A shows a display module that is onboard the retinal imaging device, in an illustrative implementation of this invention. The display module comprises a projector 901 and relay optics 902. The projector 901 projects a set of light rays, which are relayed by the relay optics 902 to the eye 903 of a user. The light rays form a visual pattern that provides visual cues, which help the user properly position the user's eye for retinal imaging (i.e., to capture images of the retina). The relay optics 902 include multiple optical elements (e.g., 911, 912), such as lenses or mirrors.

In FIG. 9A, the projector 901 is configured such that a pupil display image 905 (as defined herein) and a retina display image 907 (as defined herein) are produced inside the projector 901.

In FIG. 8, the optics of the retinal imaging device are such that a retina display image 750 (as defined herein) forms inside the retinal imaging device.

As used herein, a "retina display image" means an image that is the same (except for any rotation, flip or scaling) as an image that is formed at a retina of a user by light rays from a retinal imaging device.

As used herein, a "pupil display image" means an image that is the same (except for any rotation, flip or scaling) as an image that is formed at the pupil of a user by light rays from a retinal imaging device.

Many different types of projectors may be used in this invention.

FIGS. 9B to 9F show examples of a projector that is part of the display module, in illustrative implementations of this invention. The display module is onboard the retinal imaging device.

In FIGS. 9B to 9F, the projector is backlit by a light source (not shown in those Figures) that is in the rear of the projector. This backlight produces light rays that travel through, and then are emitted from, the projector. The light rays form a visual pattern, which provides visual cues that help the user properly position the user's eye for retinal imaging (i.e., to capture images of the retina).

In the example shown in FIG. 9B, the projector 910 includes two spatial light modulators (SLMs) 911, 912 that produce a set of light rays. The two SLMs 911, 912 are each perpendicular to the optical axis of the projector 910. A lens 914 is positioned at its focal length f from the front SLM 911. A retina display image is formed at the front SLM 911. A pupil display image 916 is formed in front of lens 914.

In the example shown in FIG. 9C, the projector 920 includes a lenslet array 921 and an SLM 922 that together produce a set of light rays. The lenslet array 921 and SLM 922 are each perpendicular to the optical axis of the projector 910. A lens 924 is positioned at its focal length f from the lenslet array 921. A retina display image is formed at the lenslet array 921. A pupil display image 926 is formed in front of lens 924.

In the example shown in FIG. 9D, the projector 930 includes a pinhole array 931 and a sub-image mask 932 that together produce a set of light rays. The pinhole array may comprise a static pinhole mask or another SLM, such as a liquid crystal display (LCD). The pinhole array 931 and sub-image mask 932 are each perpendicular to the optical axis of the projector 930. A pupil display image forms at the pinhole array 931.

In the example shown in FIG. 9E, the projector 940 includes a lenslet array 941 and a sub-image mask 942 that together produce a set of light rays. The lenslet array 941 and sub-image mask 942 are each perpendicular to the optical axis of the projector 940. A pupil display image forms at the lenslet array 941.

In the example shown in FIG. 9F, the projector 950 includes a front SLM 951 and a lens 964. The lens 964 is at its focal length f from the plane in which the retinal display image occurs. A pupil display image forms at the front SLM 951.

In FIGS. 9D and 9E, the sub-image mask includes a set of sub-image regions. In some cases, the sub-image regions are the same size as each other. In some cases, the sub-image regions each have a similar optical pattern. If the sub-image mask is paired with a pinhole mask, then for each of these regions in the sub-image mask, there is a corresponding pinhole in the pinhole mask. If the sub-image mask is paired with a lenslet array, then for each of these regions in the sub-image mask, there is a corresponding lenslet in the lenslet array.

FIGS. 10A-10C show examples of hardware for producing a light field, in illustrative implementations of this invention.

In the example shown in FIGS. 10A and 10B, two SLMs produce a light field. A diffuse light source 1001 backlights the two SLMs 1002, 1003. Light rays (e.g., 1004, 1005) originate at the diffuse light source 1001, pass through the two SLMs 1002, 1003, and are emitted by the SLMs. The pair of SLMs are configured such that, together, they emit light rays that travel in different directions.

In the example shown in FIG. 10A: (a) ray 1004 travels at angle K relative to a reference direction; (b) ray 1005 travels at angle L relative to the reference direction; and (c) angles K and L are not equal to each other.

In FIGS. 9B, 9C, 9F, 10A and 10B, each SLM (e.g., 911, 912, 922, 1002, 1003): (a) may comprise any type of spatial light modulator, including a static mask or an LCD; and (b) may produce any pattern of attenuation at a given time. For example, the pattern of attenuation may be a binary or grayscale pattern that comprises light and dark shapes that are rectangular or sinusoidal. Or, for example, the pattern of attenuation may be a pinhole pattern.

In the example shown in FIG. 10C, a lenslet array produces a light field. The lenslet array 1011 is backlit by a light source 1010, such as a diffuse light source or an LCD. The lenslet array 1011 is positioned at its focal length $f_l$ from light source 1010. A first set of light rays 1012 (that are parallel to each other) exits a first lenslet in the lenslet array 1011. A second set of light rays 1014 (that are parallel to each other but not to ray bundle 1012) exits a second lenslet in the lenslet array 1011.

It is often desirable to use relay optics to relay the light rays produced by the projector. For example, in FIG. 11, relay optics 1102 relay light from the projector 1101 to the eye 1103. The relay optics 1102 include three lenses 1111, 1112, 1114. For example, light may travel via paths 1121, 1122, 1123, 1124 through the relay optics to the eye 1103. (In FIG. 11, the lenses appear to be lines. In actuality, each lens has a thickness).

In some implementations, feedback from a sensor is used to control the display produced by the retinal imaging device.

Figure 12A:
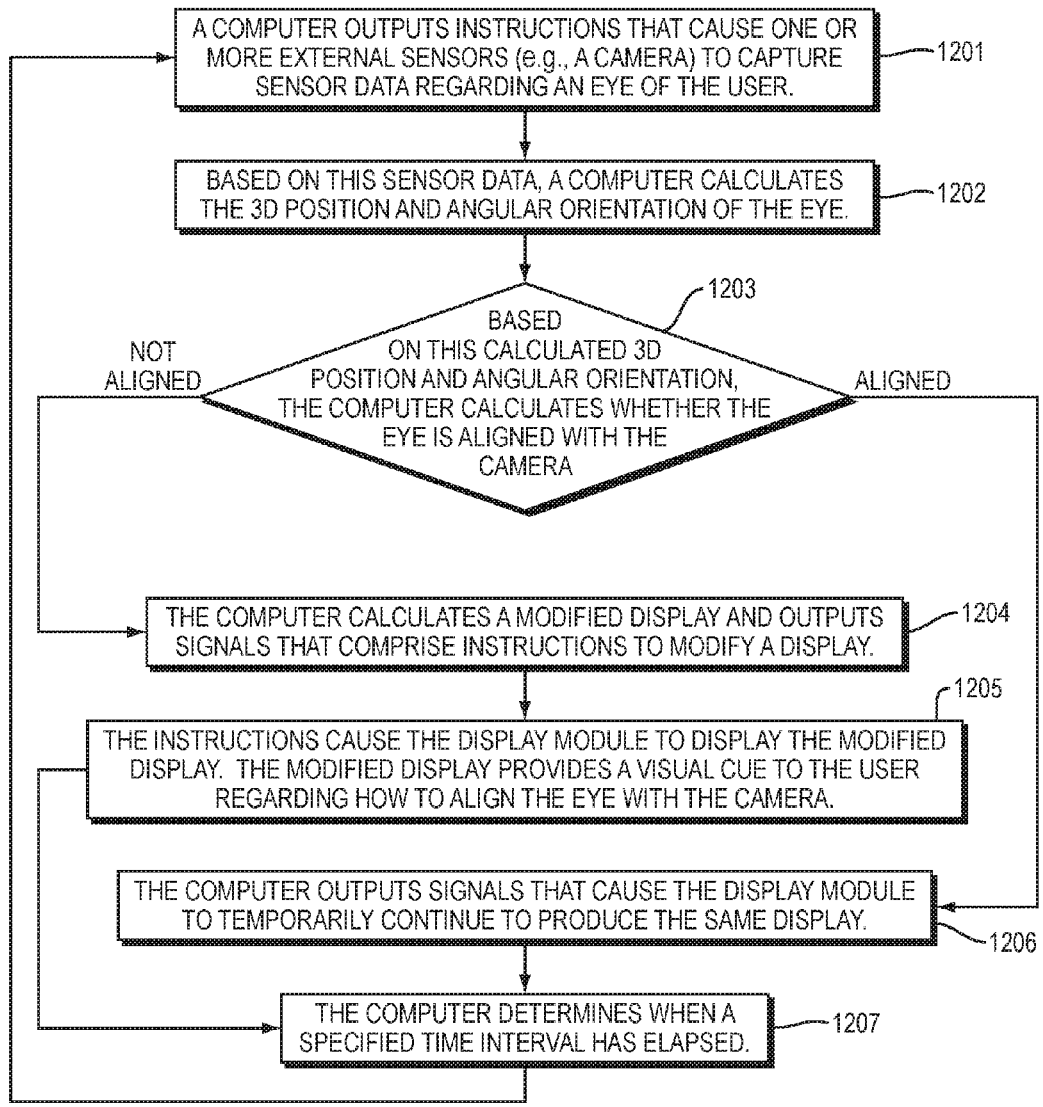
FIG. 12A is a flow-chart, for a method in which sensors provide feedback that helps control the display module.

For example, the method shown in FIG. 12A includes the following steps: A computer outputs instructions that cause one or more external sensors (e.g., a camera) to capture sensor data regarding an eye of the user (step 1201). Based on this sensor data, a computer calculates the 3D position and angular orientation of the eye (step 1202). Based on this calculated 3D position and angular orientation, the computer calculates whether the eye is aligned with the camera. If aligned, go to step 1206. If not aligned, go to step 1204 (step 1203). The computer calculates a modified display and outputs signals that comprise instructions to modify a display. The instructions cause the display module to display the modified display (step 1204). The modified display provides a visual cue to the user regarding how to align the eye with the camera. Then go to step 1207 (step 1205). The computer outputs signals that cause the display module to temporarily continue to produce the same display (step 1206). The computer determines when a specified time interval has elapsed (step 1207). After step 1207, the algorithm returns to step 1201.

In some implementations, a user provides feedback to a retinal imaging device.

Figure 12B:
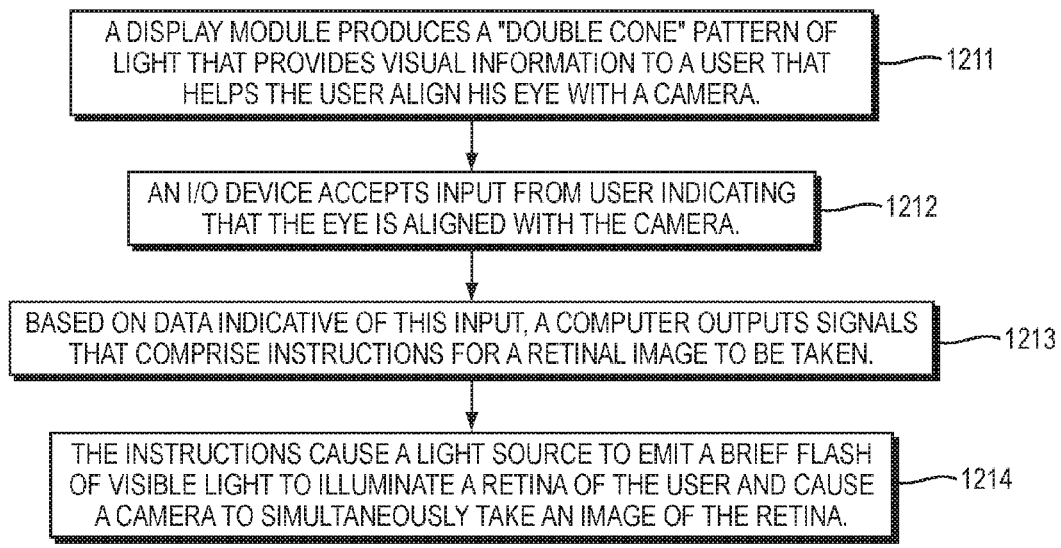
FIG. 12B is a flow-chart, for a method in which a user provides feedback to a retinal imaging device.

For example, the method shown in FIG. 12B includes the following steps: A display module produces a "double cone" pattern of light that provides visual information to a user that helps the user align his eye with a camera (step 1211). An I/O device accepts input from user indicating that the eye is aligned with the camera (step 1212). Based on data indicative of this input, a computer outputs signals that comprise instructions for a retinal image to be taken (step 1213). The instructions cause a light source to emit a brief flash of visible light to illuminate a retina of the user and cause a camera to simultaneously take an image of the retina (step 1214).

Optical Model

It is useful to model the retinal imaging device using geometrical optics and the thin lens approximation. At a plane along the optical axis, parameterize the set of rays with two dimensions of space (x,y) and two dimensions of direction (u,v), where u=tan(θ) and v=tan(φ) are the conversions of the rays from spherical coordinates. The light field at the retinal plane l(x,y,u,v) relates to the illumination path and imaging system by a coordinate transformation. As used herein, the "retinal plane" means the geometric plane at which light would strike the retina, if the retina were planar and the eye did not refract light.

To simplify analysis, it is helpful to use one spatial dimension and consider a 2D light field, l(x,u), moving through the system. This leads to a set of operations that may be performed using basic optical components. First, the light field at some distance, d, along the optical axis, may be described by the free space propagation operator:

$$S_d = \begin{bmatrix} 1 & d \\ 0 & 1 \end{bmatrix} \quad \text{Equation 1}$$

This matrix describes a shear in the 2D light field in 1D space, where rays in free space do not change direction and continue the direction they were headed. The spherical thin lens operator may describe another shear operation in u:

$$L_f = \begin{bmatrix} 1 & 0 \\ -1/f & 1 \end{bmatrix} \quad \text{Equation 2}$$

where f is the focal length of the lens.

An aperture that blocks rays in an area in space, Ω, extinguishes rays over the entire u dimension. This is described by the pupil operator, P.

$$P_\Omega(l) \rightarrow l(x_\Omega, u) = 0 \quad \text{Equation 3}$$

This notation may be used to describe light entering the eye and illuminating the retina. The light field at the cornea, $l_c$, is refracted by the cornea, stopped by the pupil, further refracted by the lens, and travels to the retina. In order to address spatial degrees of freedom for alignment, a ray based approach is used.

In some cases, a single ray cone display is employed. Specifically, a display module creates a ray of cones along the marginal rays of a focused beam. This is very effective for aligning the eye in lateral directions (x,y), but it does not fully address the problem of alignment in depth (z).

In order to help align the eye in depth z, the display module also produces another set of converging rays, which when combined with a single ray cone becomes a double ray cone.

The marginal rays that describe a ray cone have an angle of extent, $\alpha$. The eye box for this illumination source, $\omega_e$, may be found as a function of z:

$$\omega_e(z) = P_D - 2|z - z_0|u_\alpha \quad \text{Equation 4}$$

where for an extended angle, $\alpha$, $u = \tan(\alpha/2)$ and $P_D$ is the diameter of the subject's pupil.

To find the maximum axial distance from the eye, $z_r$:

$$z_r = \frac{P_D}{2u_\alpha} \quad \text{Equation 5}$$

In some implementations of this invention, the following design considerations apply: To achieve a full field of view, it is desirable for the marginal rays of the illumination beam pass the pupil. It is also desirable for the marginal rays to be distinct from the rest of the rays entering the pupil to indicate to the user that they have made it through.

A solution is to produce only the marginal rays of the illumination. If the user sees them, then the system is well aligned. Preferably, the eye box of the display is further limited to avoid situations where the marginal rays may scatter off the edge of the pupil. To this end, it is desirable to produce a set of rays that produces an eye box that is smaller than the illumination eye box, $\omega_e$. In some cases, this set of rays is:

$$l_c = \begin{pmatrix} \frac{P_D}{2} & \frac{P_D}{2} & -\frac{P_D}{2} & -\frac{P_D}{2} \\ -u_1 & u_2 & u_1 & -u_2 \end{pmatrix} \quad \text{Equation 6}$$

where $P_D$ is the user's pupil diameter and $(u_1, u_2)$ are two sufficiently distinct ray angles that make it through the imaging system.

The set of rays defined by Equation 6 represent a double ray cone pattern with ray intersections at different distances from the eyepiece. As such, to define the eye box of this design, take the intersection of Equation 4 applied to $u_1$ and $u_2$.

The display optics may be described by combining Equations 1 and 2 for each optical element, which produces a 2×2 ray transfer matrix T for the 2D light field case.

$$T = S_1 L_1 S_2 L_2 \ldots S_n L_n \quad \text{Equation 7}$$

The light field at the display, $l_d$, propagates through the optical system, and produces a light field at the eye pupil $l_c = T l_d$. This equation may be solved for the desired light field at the display, ensuring that the resulting light field clears the system's exit pupil $P_E$.

$$l_d = T^{-1} l_c \quad \text{Equation 8}$$

Prototype

The following six paragraphs describe a prototype of this invention. This prototype is a non-limiting example; this invention may be implemented in many other ways.

In this prototype, an ophthalmic objective lens focuses light through the pupil and forms an image of the retina. A beamsplitter produces a pupil-forming display in the optical axis.

In this prototype, a 40D ophthalmic lens comprises the objective lens of the camera and is positioned at the front of the device. This lens relays the retinal plane from within the eye to a plane behind the lens.

Illumination: In this prototype, the white light illumination for the retina is collimated cross-polarized illumination. A point source of light is employed (instead of an annular pattern) to facilitate imaging without dilation drop. A 4000K white LED is controlled by a flash driver, and is connected to an Arduino® Micro microcontroller using an I²C (inter-integrated circuit). The Arduino® Micro is connected to a laptop, and a C++ controller program sends flash trigger signals over USB. In normal operation, the flash driver is set to produce one 10 ms flash per exposure with an illumination energy of $$81 \times 10^{-6} \frac{\text{Joules}}{\text{cm}^2}$$

incident on an aphakic eye in the worst case, which is over 3 orders of magnitude below the maximum permissible exposure (MPE) limits for Maxwellian illumination sources (ISO 15004-2:2007 and ISO 10940:2009).

In this prototype, the LED is placed behind a pair of lenses that relay its image one focal length away from a 25 mm focal length plano-convex condenser lens (Edmund Optics® #45-097). The collimated beam is inserted into the imaging path with a polarizing beamsplitter. A linear polarizer is placed in front of the light source and is configured so that the polarizing beam splitter only allows light with a different polarization state back through the system. This cross polarized configuration reduces undesirable specular reflections.

Display: In this prototype, the display path is inserted into the illumination path before the condenser lens by a 90T/10R plate beamsplitter. The beamsplitter is followed by a 50 mm magnifier lens which produces a plane conjugate to the retina. The 90T/10R beamsplitter behaves as the exit pupil of the display system, defining the eye box of the display plane. A pair of printed transparency masks are placed 12 mm apart, with the closest mask one focal length from the magnifier lens.

Imaging: In this prototype, a USB camera (Point Grey® FMVU-13S2C) with a 16 mm c-mount lens is placed behind the polarizing beamsplitter and focused on the retinal image plane. A C++ program running on the connected laptop synchronizes the shutter and illumination triggers.

This invention may be implemented in many different ways, and is not limited to the prototype described in the preceding six paragraphs.

More Details

In illustrative implementations, a handheld retinal imaging device provides visual cues for eye alignment, enabling a user to employ the device to capture images of the retina of one or his or her own eyes. Such "selfie" retinal imaging has many practical advantages, including for diagnostic and preventive medicine. Retinal images captured with this invention may be analyzed: (a) to detect changes in retinal vasculature morphology that are indicative of health status; (b) to diagnose eye diseases such as glaucoma, age-related macular degeneration, and diabetic retinopathy; and (c) to detect risk factors for heart disease, stroke, Alzheimer's disease, and multiple sclerosis.

In illustrative implementations, a retinal imaging device includes a projector. The projector produces light rays that form a visual fixation pattern. The user moves his head/eye relative to the retinal imaging device in order to achieve a better view of the fixation pattern. When the fixation pattern is fully visible to the user's eye without distortion, the user's eye is properly positioned for retinal imaging (e.g., is at an optimal lateral (x,y) and depth (z) wise position of the eye for image centering and focus).

In illustrative implementations, the retinal imaging device is handheld or otherwise highly portable.

In illustrative implementations, a near eye alignment display achieves tighter eye box control which enables precise self-alignment of the eye. The alignment display produces light rays that pass through points in the pupil that are adjacent to the perimeter of the pupil. As a result, pupil misalignment produces a different perceived image to the user.

In illustrative implementations, an interactive "ray-cone" display facilitates self-alignment of eyes.

In illustrative implementations, an individual uses an alignment dependent perceptual cue to self-direct the positioning of their eye. The user moves his or her eye in front of the device, and perceives a different image depending on if the user is laterally off center, too close, or too far. This alignment display has applications in which eye alignment is critical, such as in head mounted displays, ophthalmology, or survey sighting.

In illustrative implementations, complex eye alignment tasks are simplified by exploiting user interaction. Applications for this invention include wearable technologies, such as in augmented reality, virtual reality, and quantified self and predictive health devices.

In illustrative implementations, the device uses a perceptual cue to enable the user to align themselves to an object.

In illustrative implementations, a computer performs (or has performed) an algorithm to generate a perceptual cue.

In illustrative implementations, this alignment dependent display allows lateral, axial, and rotational alignment of the eye to the imaging system.

In some cases, the device allows the patient to perform the alignment himself or herself, making this method user guided. In some cases, the device uses external sensors, and feedback from these sensors helps alignment by changing the cue for the user.

In illustrative implementations, a projector with a small enough space-bandwidth product (SBP), or a projector with high enough angular and spatial resolution, is used to generate the perceptual cues necessary to enable eye alignment.

In some implementations, layered transparencies offset axially generate a light field.

For a given set pupil size, either measured or estimated, a set of rays exists which are blocked by the pupil of the eye unless the eye is in the correct position. Additionally, this set of rays is imaged onto the retina by the eye's optical system in a way which ensures a single ray reaches a unique location on the retina.

In some implementations, the ability to control where on the retina the rays are imaged allows multiple perceptual "regions" to be designed so that a particular set of points is only visible to the user when the eye is in a particular region.

In some implementations, a computer performs an algorithm to determine the rays needed to define the set of alignment regions. Hardware is used to implement such rays.

In some implementations of this invention, a retinal imaging system has one or more of the following features (a) to (k):

(a) the system facilitates self-alignment of the eye to an imaging system, such as an improved viewfinder for macro photography;

(b) the system may be used for ophthalmic imaging such as alignment to retina or anterior segment imaging systems;

(c) the system may be implemented as a bi-ocular handheld form factor for user alignment;

(d) the system may be used as an alignment cue when mounting or calibrating HMDs;

(e) the system may be used for user positioning for biometric applications in which features are mechanically coupled to the head (e.g., face, eye, ear, mouth, nose, hair);

(f) the system may be configured for self-measurement (by a human user using the system) of interpupillary distance (IPD).

(g) the system may be configured for self-measurement (by a human user using the system) of pupil size.

(h) the time to alignment and quality of alignment may be measured using external sensors, indicating cognitive arousal or impairment;

(i) the system may combine perceptual cues with external sensors, such as light time of flight (TOF) distance sensors to improve alignment capability;

(j) TOF sensors may be arranged around the display to estimate the fine location of the eye, and the display may modify its displayed pattern to improve user interaction;

(k) a set of rays used to generate the perceptual cue may be generated through a variety of different optical methods. For example, in some implementations, the display creates a high spatial frequency image at the focal plane which helps control user accommodation. Moving the perceived location of this object (optically or physically) allows control of user accommodation at different focal depths.

Computers

In exemplary implementations of this invention, one or more electronic computers (e.g. 811, 812) are programmed and specially adapted: (1) to control the operation of, or interface with, hardware components of a retinal imaging device, including any light source, any projector, any camera, any other sensor, and any display module; (2) to synchronize illumination by a light source and image capture by a camera; (3) to adjust the operation of a retinal imaging device in response to user input, including by causing a camera to capture an image; (4) to adjust the operation of a retinal imaging device in response to feedback from a sensor (such as sensor data regarding eye position); (5) to control a display module such that the display module outputs visual cues that facilitate alignment of an eye; (6) to perform any image processing or computer vision algorithm, (7) to perform any other calculation, computation, program, algorithm, or computer function described or implied above; (8) to receive signals indicative of human input; (9) to output signals for controlling transducers for outputting information in human perceivable format; and (10) to process data, to perform computations, to execute any algorithm or software, and to control the read or write of data to and from memory devices (items 1-10 of this sentence referred to herein as the "Computer Tasks"). The one or more computers may be in any position or positions within or outside of the retinal imaging device. For example, in some cases (a)

at least one computer is housed in or together with other components of the retinal imaging device, such as the camera, and (b) at least one computer is remote from other components of the retinal imaging device. The one or more computers communicate with each other or with other components of the retinal imaging device either: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied above. For example, in some cases, instructions encoded in a tangible, non-transitory, computer-accessible medium comprise instructions for a computer to perform the Computer Tasks.

Network Communication

In illustrative implementations of this invention, an electronic device (e.g., 815, 801, 803, 811, 812) is configured for wireless or wired communication with other electronic devices in a network.

For example, in some cases, a retinal imaging device 800 and an external computer 812 each include a wireless communication module for wireless communication with other electronic devices in a network. Each wireless communication module (e.g., 810, 840) includes (a) one or more antennas, (b) one or more wireless transceivers, transmitters or receivers, and (c) signal processing circuitry. The wireless communication module receives and transmits data in accordance with one or more wireless standards.

In some cases, one or more of the following hardware components are used for network communication: a computer bus, a computer port, network connection, network interface device, host adapter, wireless module, wireless card, signal processor, modem, router, computer port, cables or wiring.

In some cases, one or more computers (e.g., 810, 811) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

DEFINITIONS

The terms "a" and "an", when modifying a noun, do not imply that only one of the noun exists.

The "apex angle" at which a light ray converges to the apex of a cone means the angle between the central axis of the cone and the light ray.

To compute "based on" specified data means to perform a computation that takes the specified data as an input.

Here are some non-limiting examples of a "camera": (a) a digital camera; (b) a digital grayscale camera; (c) a digital color camera; (d) a video camera; (e) a light sensor or image sensor, (f) a set or array of light sensors or image sensors; (g) an imaging system; (h) a light field camera or plenoptic camera; (i) a time-of-flight camera; and (j) a depth camera. A camera includes any computers or circuits that process data captured by the camera.

To say that light has a specified "color" means that the peak wavelength of the color spectrum of the light occurs at the specified color. To say that a first color and a second color are "different" from each other means that the peak wavelength of the color spectrum of the first color differs from the peak wavelength of the color spectrum of the second color by at least 50 nanometers.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

The term "cone" means a geometric shape that is a right circular cone, which has a finite distance between apex and base. A "cone" is a so-called "solid" geometric shape, in that a cone includes points within the cone's exterior surface.

"Defined Term" means a term or phrase that is set forth in quotation marks in this Definitions section.

For an event to occur "during" a time period, it is not necessary that the event occur throughout the entire time period. For example, an event that occurs during only a portion of a given time period occurs "during" the given time period.

The term "e.g." means for example.

Non-limiting examples of "emitting" light include: (a) an LED or other solid state light source emitting light; (b) an incandescent light source emitting light; (c) a fluorescent light source emitting light; and (d) a reflector reflecting light.

Each equation above is referred to herein by the equation number set forth to the right of the equation. For example: "Equation 1" means the equation labeled Equation 1 above; "Equation 2" means the equation labeled Equation 2 above;

"Equation 3" means the equation labeled Equation 3 above; "Equation 4" means the equation labeled Equation 4 above; "Equation 5" means the equation labeled Equation 5 above; "Equation 6" means the equation labeled Equation 6 above; "Equation 7" means the equation labeled Equation 7 above; and "Equation 8" means the equation labeled Equation 8 above.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

To says that light rays "do not form" a specified image means that the light rays do not form the same image as the specified image. For example, light rays that form only a distorted or truncated version of a specified image do not form the specified image.

"For instance" means for example.

In the context of a camera, "front" is optically closer to the scene being imaged, and "rear" is optically farther from the scene, during normal operation of the camera. In the context of a display device, "front" is optically closer to a human viewer, and "rear" is optically farther from the viewer, when the viewer is viewing a display produced by the device during normal operation of the device. The "front" and "rear" of a display device continue to be the front and rear, even when no viewer is present.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"I/O device" means an input/output device. Non-limiting examples of an I/O device include a touch screen, other electronic display screen, keyboard, mouse, microphone, handheld electronic game controller, digital stylus, display screen, speaker, or projector for projecting a visual display.

In the context of an apparatus that includes a camera, "lateral direction" means a direction that perpendicular to the optical axis of the camera.

"Lens" means a single lens, compound lens or set of lenses. For example, an achromatic doublet is a lens.

To say that a light ray "lies on" a surface of a cone means that at least part of the path of the ray is parallel to and spatially coincides with the surface.

"Light" means electromagnetic radiation of any frequency. For example, "light" includes, among other things, visible light and infrared light. Likewise, any term that directly or indirectly relates to light (e.g., "imaging") shall be construed broadly as applying to electromagnetic radiation of any frequency.

To say that an eye is focused at "optical infinity" means that the eye is focused such that parallel light rays that enter the eye focus to a single point on the retina.

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

The "peak wavelength" of a color spectrum of light means the wavelength at which the greatest amplitude of the light occurs.

The term "projector" means a device that emits light rays.

"Pupillary plane" means a geometric plane that intersects a pupil of an eye and that is perpendicular to the optical axis of the eye.

"Retinal image" means a digital image of a retina, which image is captured by a camera.

As used herein, the term "set" does not include a group with no elements. Mentioning a first set and a second set does not, in and of itself, create any implication regarding whether or not the first and second sets overlap (that is, intersect).

"Some" means one or more.

"Spatial light modulator" and "SLM" each mean a device (i) that transmits light through the device or reflects light from the device, and (ii) that causes a modulation of the intensity, frequency, phase or polarization state of light transmitted through or reflected from the device, such that the modulation depends on the spatial position at which the light is incident on the device.

As used herein, a "subset" of a set consists of less than all of the elements of the set.

"Substantially" means at least ten percent. For example: (a) 112 is substantially larger than 100; and (b) 108 is not substantially larger than 100.

The term "such as" means for example.

"3D" means three dimensional.

To say that a machine-readable medium is "transitory" means that the medium is a transitory signal, such as an electromagnetic wave.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) different steps, out of the steps in the method, occur a different number of times during the method, (4) any combination of steps in the method is done in parallel or serially; (5) any step or steps in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses. In each case described in this paragraph, the Applicant or Applicants are acting as his, her, its or their own lexicographer.

Variations

This invention may be implemented in many different ways. Here are some non-limiting examples:

In some implementations, this invention is an apparatus comprising: (a) a camera; (b) a light source; (c) a projector for emitting a first set of light rays and a second set of light rays, such that: (i) the first set of light rays lies on an exterior surface of a first cone, (ii) the second set of light rays lie on an exterior surface of a second cone, (iii) a first 3D region exists, which region is the intersection of the first and second cones, (iv) when a pupil of an eye of a user is positioned in the region and the eye is looking at the camera, the first and second set of light rays form a first image on the retina of the eye, and (v) when the pupil is not positioned in the region, the first and second set of light rays do not form the first image on the retina; (d) an I/O device for receiving, from the user, input indicating that the user is seeing the first image; and (e) one or more computers for outputting, based on the input, instructions (i) for the camera to capture one of more retinal images of the retina, and (ii) for the light source to illuminate the retina while the camera captures the retinal images. In some cases: (a) the projector is configured to emit light that has a first color; (b) the light source that illuminates the retina is configured to emit light that has a second color; and (c) the first and second colors are different from each other. In some cases: (a) the apparatus further comprises (i) one or more sensors for gathering sensor data indicative of location of the eye, and (ii) an electronic screen for displaying a visual display that is visible to the user; and (b) the one or more computers are programmed (i) to calculate, based on the sensor data, one or more spatial coordinates of a point in the eye, and (ii) to output, based on the one or more spatial coordinates, instructions to modify the visual display. In some cases, the visual display includes a symbol that indicates a direction of movement, which direction is towards the first 3D region. In some cases, the projector is configured to emit the first and second sets of light rays such that, when the eye is looking toward the camera and the pupil is in a second 3D region that does not overlap with the first 3D region, a second image forms on the retina, which second image is different than the first image. In some cases, the second image comprises a distorted version of the first image. In some cases, the second image comprises a truncated version of the first image. In some cases, when the pupil is in the first 3D region and the eye is looking toward the camera and is focused at optical infinity, each light ray in the first and second sets of rays strikes the retina at a retinal location, which retinal location is different than any other location at which any other ray in the first and second sets strikes the retina. In some cases, when the pupil is in the first 3D region and the eye is looking toward the camera and is focused at optical infinity, each light ray in the first and second sets of rays also strikes the pupil at a pupil location, which pupil location is different than any other location at which any other ray in the first and second sets strikes the pupil. In some cases: (a) the first set of light rays converges to an apex of the first cone, at a first apex angle; (b) the second set of light rays converges to an apex of the second cone, at a second apex angle; and (c) the first and second apex angles are different from each other. Each of the cases described above in this paragraph is an example of the apparatus described in the first sentence of this paragraph, and is also an example of an embodiment of this invention that may be combined with other embodiments of this invention.

In some implementations, this invention is a method comprising, in combination: (a) a projector emitting a first set of light rays and a second set of light rays, such that (i) the first set of light rays lies on an exterior surface of a first cone, (ii) the second set of light rays lie on an exterior surface of a second cone, (iii) a first 3D region exists, which region is the intersection of the first and second cones, (iv) when a pupil of an eye of a user is positioned in the region and the eye is looking at a camera, the first and second set of light rays form a first image on the retina of the eye, and (v) when the pupil is not positioned in the region, the first and second set of light rays do not form the first image on the retina; (b) an I/O device receiving, from the user, input indicating that the user is seeing the first image; and (c) one or more computers outputting, based on the input, instructions (i) for the camera to capture one of more retinal images of the retina, and (ii) for a light source to illuminate the retina while the camera captures the retinal images. In some cases: (a) the projector emits light that has a first color; (b) the light source that illuminates the retina emits light that has a second color; and (c) the first and second colors are different from each other. In some cases: (a) one or more sensors gather sensor data indicative of location of the eye; (b) an electronic screen displays a visual display that is visible to the user; and (c) the one or more computers (i) calculate, based on the sensor data, one or more spatial coordinates of a point in the eye, and (ii) output, based on the one or more spatial coordinates, instructions to modify the visual display. In some cases, the visual display includes a symbol that indicates a direction of movement, which direction is towards the first 3D region. In some cases: (a) a second 3D region exists, which does not overlap with the first 3D region; and (b) when the pupil is located in a second 3D region and the eye is looking toward the camera, a second image forms on the retina, which second image is different than the first image. In some cases, the second image comprises a distorted version of the first image. In some cases, the second image comprises a truncated version of the first image. In some cases, when the pupil is in the first 3D region and the eye is looking toward the camera and is focused at optical infinity, each light ray in the first and second sets of rays strikes the retina at a retinal location, which retinal location is different than any other location at which any other ray in the first and second sets strikes the retina. In some cases, when the pupil is in the first 3D region and the eye is looking toward the camera and is focused at optical infinity, each light ray in the first and second sets of rays also strikes the pupil at a pupil location, which pupil location is different than any other location at which any other ray in the first and second sets strikes the pupil. In some cases: (a) the first set of light rays converges to an apex of the first cone, at a first apex angle; (b) the second set of light rays converges to an apex of the second cone, at a second apex angle; and (c) the first and second apex angles are different from each other. Each of the cases described above in this paragraph is an example of the method described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the abovementioned implementations, embodiments and features.

What is claimed is:

1. An apparatus comprising:
   (a) a camera;
   (b) a light source;
   (c) a projector for emitting a first set of light rays and a second set of light rays, such that:
       (i) the first set of light rays lies on an exterior surface of a first cone,
       (ii) the second set of light rays lie on an exterior surface of a second cone,
       (iii) a first 3D region exists, which region is the intersection of the first and second cones,
       (iv) when a pupil of an eye of a user is positioned in the region and the eye is looking at the camera, the first and second set of light rays form a first image on the retina of the eye, and
       (v) when the pupil is not positioned in the region, the first and second set of light rays do not form the first image on the retina;
   (d) an I/O device for receiving, from the user, input indicating that the user is seeing the first image; and
   (e) one or more computers for outputting, based on the input, instructions
       (i) for the camera to capture one of more retinal images of the retina, and
       (ii) for the light source to illuminate the retina while the camera captures the retinal images.

2. The apparatus of claim 1, wherein:
   (a) the projector is configured to emit light that has a first color;
   (b) the light source that illuminates the retina is configured to emit light that has a second color; and
   (c) the first and second colors are different from each other.

3. The apparatus of claim 1, wherein:
   (a) the apparatus further comprises
       (i) one or more sensors for gathering sensor data indicative of location of the eye, and
       (ii) an electronic screen for displaying a visual display that is visible to the user; and
   (b) the one or more computers are programmed
       (i) to calculate, based on the sensor data, one or more spatial coordinates of a point in the eye, and
       (ii) to output, based on the one or more spatial coordinates, instructions to modify the visual display.

4. The apparatus of claim 3, wherein the visual display includes a symbol that indicates a direction of movement, which direction is towards the first 3D region.

5. The apparatus of claim 1, wherein the projector is configured to emit the first and second sets of light rays such that, when the eye is looking toward the camera and the pupil is in a second 3D region that does not overlap with the first 3D region, a second image forms on the retina, which second image is different than the first image.

6. The apparatus of claim 5, wherein the second image comprises a distorted version of the first image.

7. The apparatus of claim 5, wherein the second image comprises a truncated version of the first image.

8. The apparatus of claim 1, wherein, when the pupil is in the first 3D region and the eye is looking toward the camera and is focused at optical infinity, each light ray in the first and second sets of rays strikes the retina at a retinal location, which retinal location is different than any other location at which any other ray in the first and second sets strikes the retina.

9. The apparatus of claim 8, wherein, when the pupil is in the first 3D region and the eye is looking toward the camera and is focused at optical infinity, each light ray in the first and second sets of rays also strikes the pupil at a pupil location, which pupil location is different than any other location at which any other ray in the first and second sets strikes the pupil.

10. The apparatus of claim 1, wherein:
    (a) the first set of light rays converges to an apex of the first cone, at a first apex angle;
    (b) the second set of light rays converges to an apex of the second cone, at a second apex angle; and
    (c) the first and second apex angles are different from each other.

11. A method comprising, in combination:
    (a) a projector emitting a first set of light rays and a second set of light rays, such that
        (i) the first set of light rays lies on an exterior surface of a first cone,
        (ii) the second set of light rays lie on an exterior surface of a second cone,
        (iii) a first 3D region exists, which region is the intersection of the first and second cones,
        (iv) when a pupil of an eye of a user is positioned in the region and the eye is looking at a camera, the first and second set of light rays form a first image on the retina of the eye, and
        (v) when the pupil is not positioned in the region, the first and second set of light rays do not form the first image on the retina;
    (b) an I/O device receiving, from the user, input indicating that the user is seeing the first image; and
    (c) one or more computers outputting, based on the input, instructions
        (i) for the camera to capture one of more retinal images of the retina, and
        (ii) for a light source to illuminate the retina while the camera captures the retinal images.

12. The method of claim 11, wherein:
    (a) the projector emits light that has a first color;
    (b) the light source that illuminates the retina emits light that has a second color; and
    (c) the first and second colors are different from each other.

13. The method of claim 11, wherein:
    (a) one or more sensors gather sensor data indicative of location of the eye;
    (b) an electronic screen displays a visual display that is visible to the user; and
    (c) the one or more computers
        (i) calculate, based on the sensor data, one or more spatial coordinates of a point in the eye, and (ii) output, based on the one or more spatial coordinates, instructions to modify the visual display.

14. The method of claim 13, wherein the visual display includes a symbol that indicates a direction of movement, which direction is towards the first 3D region.

15. The method of claim 11, wherein:
   (a) a second 3D region exists, which does not overlap with the first 3D region; and
   (b) when the pupil is located in a second 3D region and the eye is looking toward the camera, a second image forms on the retina, which second image is different than the first image.

16. The method of claim 15, wherein the second image comprises a distorted version of the first image.

17. The method of claim 15, wherein the second image comprises a truncated version of the first image.

18. The method of claim 11, wherein, when the pupil is in the first 3D region and the eye is looking toward the camera and is focused at optical infinity, each light ray in the first and second sets of rays strikes the retina at a retinal location, which retinal location is different than any other location at which any other ray in the first and second sets strikes the retina.

19. The method of claim 18, wherein, when the pupil is in the first 3D region and the eye is looking toward the camera and is focused at optical infinity, each light ray in the first and second sets of rays also strikes the pupil at a pupil location, which pupil location is different than any other location at which any other ray in the first and second sets strikes the pupil.

20. The method of claim 11, wherein:
   (a) the first set of light rays converges to an apex of the first cone, at a first apex angle;
   (b) the second set of light rays converges to an apex of the second cone, at a second apex angle; and
   (c) the first and second apex angles are different from each other.

\* \* \* \* \*